US010359367B2

(12) United States Patent
Fukazawa

(10) Patent No.: US 10,359,367 B2
(45) Date of Patent: Jul. 23, 2019

(54) INSPECTION APPARATUS AND INSPECTION METHOD

(71) Applicant: NIKON CORPORATION, Tokyo (JP)

(72) Inventor: Kazuhiko Fukazawa, Kamakura (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 13/663,911

(22) Filed: Oct. 30, 2012

(65) Prior Publication Data

US 2013/0114081 A1    May 9, 2013

Related U.S. Application Data

(63) Continuation of application No. PCT/JP2011/002512, filed on Apr. 28, 2011.

(30) Foreign Application Priority Data

Apr. 30, 2010 (JP) .................. 2010-105868
Apr. 30, 2010 (JP) .................. 2010-105869

(51) Int. Cl.
*G03F 7/20* (2006.01)
*G01N 21/95* (2006.01)

(52) U.S. Cl.
CPC ..... *G01N 21/9501* (2013.01); *G03F 7/70641* (2013.01)

(58) Field of Classification Search
CPC ................. G01N 21/9501; G03F 7/70641
See application file for complete search history.

(56) References Cited

U.S. PATENT DOCUMENTS 4,387,994 A * 6/1983 Balasubramanian ......... 356/513
5,555,474 A * 9/1996 Ledger .......................... 356/632
(Continued)

FOREIGN PATENT DOCUMENTS

JP      2-224319      9/1990
JP      H07-326563    12/1995
(Continued)

OTHER PUBLICATIONS

Z. Mark Ma, "Impact of Illumination Coherence and Polarization on the Imaging of Attenuated Phase Shift Masks" Sep. 14, 2001.*
(Continued)

*Primary Examiner* — Maurice C Smith
(74) *Attorney, Agent, or Firm* — Finnegan, Henderson, Farabow, Gatterr & Dunner, LLP

(57) ABSTRACT

There is provided an inspection apparatus, including: an illuminator configured to irradiate a pattern, a detector configured to detect a reflected light from the pattern, and a calculator configured to compare a first change and a second change to calculate a deviation between the first and second changes. The first change which is a change, of a detection result of a pattern formed by a plurality of first exposure conditions, with respect to the first exposure conditions. The second change which is a change, of a detection result of a reflected light, from a pattern, generated by irradiating the pattern with the illumination light. The pattern is formed by a plurality of second exposure conditions each having a predetermined interval in a range which has at least one part overlapping with a range of the first exposure conditions, with respect to the second exposure conditions.

32 Claims, 11 Drawing Sheets

(56) References Cited

U.S. PATENT DOCUMENTS

| | | | |
|---|---|---|---|
| 5,731,113 A * | 3/1998 | Ueno | G03F 7/70425 356/399 |
| 5,750,294 A | 5/1998 | Hasegawa | |
| 5,811,223 A * | 9/1998 | Bae | 430/312 |
| 5,876,883 A * | 3/1999 | Leroux | 430/22 |
| 5,981,119 A * | 11/1999 | Adams | 430/30 |
| 6,249,347 B1 | 6/2001 | Svetkoff et al. | 356/625 |
| 6,483,571 B1 * | 11/2002 | Shiraishi | 355/53 |
| 6,737,207 B2 * | 5/2004 | Imai | 430/30 |
| 6,803,178 B1 * | 10/2004 | Subramanian et al. | 430/394 |
| 6,869,807 B2 | 3/2005 | Yoshitake et al. | |
| 7,273,685 B2 * | 9/2007 | Sasazawa et al. | 430/30 |
| 7,879,516 B2 * | 2/2011 | Kawachi et al. | 430/30 |
| 8,144,970 B2 | 3/2012 | Miyashita | |
| 2002/0111038 A1 * | 8/2002 | Matsumoto | G03F 7/70458 438/763 |
| 2003/0048458 A1 * | 3/2003 | Mieher et al. | 356/601 |
| 2003/0104292 A1 | 6/2003 | Tomimatu | |
| 2003/0170552 A1 | 9/2003 | Miyashita | |
| 2005/0125178 A1 * | 6/2005 | Komine | G03F 7/70441 702/85 |
| 2005/0190381 A1 * | 9/2005 | Mui | G01B 11/0616 356/630 |
| 2006/0098189 A1 | 5/2006 | Oomori et al. | |
| 2006/0199089 A1 | 9/2006 | Watanabe et al. | |
| 2006/0234136 A1 * | 10/2006 | Kim | 430/5 |
| 2006/0292460 A1 * | 12/2006 | Sato et al. | 430/5 |
| 2007/0128529 A1 * | 6/2007 | Kazaana | G03F 7/70525 430/30 |
| 2012/0324407 A1 * | 12/2012 | Matsunawa | G03F 7/705 716/55 |

FOREIGN PATENT DOCUMENTS

| | | | |
|---|---|---|---|
| JP | 2002-353104 | | 12/2002 |
| JP | 2003-142397 | | 5/2003 |
| JP | 2003-168641 | | 6/2003 |
| JP | 2006-186177 | | 7/2006 |
| JP | 2006-216865 | | 8/2006 |
| JP | 2007-303905 A | | 11/2007 |
| JP | 2007-304054 | | 11/2007 |
| JP | WO2009/091034 | * 1/2009 | G01N 21/956 |
| JP | 2009-204313 | | 9/2009 |
| JP | 2010-48604 A | | 4/2010 |
| WO | WO2007/069457 | | 6/2007 |
| WO | WO2009/091034 | | 7/2009 |

OTHER PUBLICATIONS

Xinhui Niu, "Specular Spectroscopic Scatterometry" May 2, 2001.*

Mary B. Chan, "Fabrication of large SU-8 mold with high aspect ratio microchannels by UV exposure dose reduction", p. 177, Apr. 14, 2004.*

International Search Report dated Jun. 14, 2011, from the Japan Patent Office in PCT/JP2011/002512.

International Preliminary Examination Report on Patentability issued for International Application No. PCT/JP2011/002512, dated Jun. 14, 2011.

Official Action issued by Japanese Patent Office dated Nov. 11, 2014 in the counterpart Japanese Application No. 2012-512679, and English translation thereof.

Office Action issued by the State Intellectual Property Office of People's Republic of China in counterpart Application No. 201180021893.2 dated Feb. 3, 2015, and English translation thereof, 12 pages.

Official Action issued by Japanese Patent Office dated Mar. 10, 2015 in the counterpart Japanese Application No. 2012-512679, and English translation thereof.

Notice Of Preliminary Rejection issued by the Korean Intellectual Property Office in Korean Application No. 10-2012-7028507, dated Nov. 22, 2016 (7 pages).

* cited by examiner

INSPECTION APPARATUS AND INSPECTION METHOD

CROSS-REFERENCE TO RELATED APPLICATIONS

This is a Continuation Application of International Application No. PCT/JP2011/002512 filed on Apr. 28, 2011 which claims priorities to Japanese Patent Applications No. 2010-105868 and No. 2010-105869 both filed on Apr. 30, 2010. The contents of the aforementioned applications are incorporated herein by reference in their entirety.

BACKGROUND

Field of the Invention

The present invention relates to an inspection apparatus and an inspection method for inspecting a semiconductor substrate exposed by an optical exposer.

Description of the Related Art

As a method for finding an optimal focus condition and an optimal dose amount (exposure amount) of an optical exposer, there has been known a method for using a wafer (hereinafter, referred to as an FEM wafer) which is exposed by the optical exposer while changing the focus and the dose amount for each shot (for example, see Japanese Patent Application Laid-Open No. 2007-304054). In this method, for example, in a case that a line pattern is exposed and projected to a surface of the FEM wafer, a spot at which the profile (line width) of the pattern changes depending on change of the focus is measured by an electron microscope (CD-SEM); and it is found a graph (hereinafter, referred to as a line-width reference focus curve) showing change of the line width (vertical axis) with respect to change of the focus (horizontal axis). Here, a focus value having a maximum line width is defined as the best focus; and it is found the focus value having the maximum line width in the line-width reference focus curve. In particular, a plurality of line widths, each depending on change of the focus in the same dose amount, are measured; the line-width reference focus curve is found by using an average value of the measured line widths; and the focus value having the maximum line width in the line-width reference focus curve is found as the optimal focus condition (best focus) of the optical exposer.

Further, a spot at which the profile (line width) of the pattern changes depending on change of the dose amount is measured by the electron microscope (CD-SEM); and it is found a graph (hereinafter, referred to as a line-width reference dose curve) showing change of the line width (vertical axis) with respect to change of the dose amount (horizontal axis). Then, a dose amount, in which a line width of a setting value can be found in the line-width reference dose curve, is obtained as the optimal dose amount (best dose amount) of the optical exposer.

SUMMARY

According to an aspect of the present teaching, there is provided that an inspection apparatus, including:
an illuminator configured to irradiate a pattern formed by an exposure with an illumination light;
a detector configured to detect a reflected light from the pattern to which the illumination light is irradiated; and a calculator configured to compare a first change which is a change, of a detection result of a pattern formed by a plurality of first exposure conditions, with respect to the first exposure conditions and a second change which is a change, of a detection result of a reflected light, from a pattern, generated by irradiating the pattern with the illumination light, the pattern being formed by a plurality of second exposure conditions each having a known predetermined interval in a range which has at least one part overlapping with a range of the first exposure conditions, with respect to the second exposure conditions; and to calculate a deviation between the first change and the second change.

DESCRIPTION OF THE EMBODIMENTS

Figure 1:
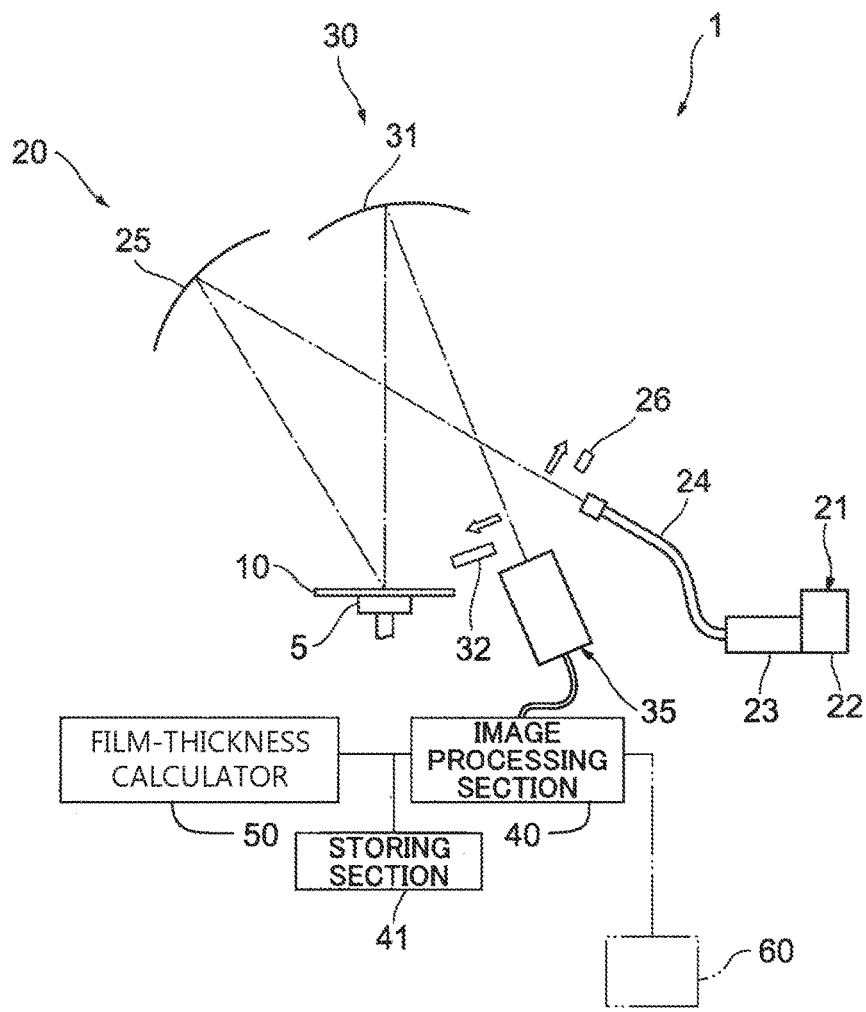
FIG. 1 shows an overall construction of a surface inspection apparatus.

Hereinbelow, referring to the accompanying drawings, an embodiment of the present teaching will be explained. FIG. 1 shows a surface inspection apparatus of this embodiment, which is utilized to inspect the surface of a semiconductor wafer 10 (to be referred to as a wafer 10 hereinbelow) which is a semiconductor substrate. As shown in FIG. 1, the surface inspection apparatus 1 of this embodiment is provided with a stage 5 configured to support the approximately disk-shaped wafer 10, which is carried therein by a carrier device (not shown) and placed on the stage 5 while being fixed and held by vacuum suction. The stage 5 supports the wafer 10 to be rotatable (within the surface of the wafer 10) with a rotational symmetrical axis of the wafer 10 (the central axis of the stage 5) as the rotation axis. Further, the stage 5 can tilt the wafer 10 about an axis along the surface of the wafer 10 (an axis substantially perpendicular to a plane contains an optical axis of an incident light and an optical axis of a reflected light), and can adjust an incidence angle of illumination light.

Further, the surface inspection apparatus 1 is configured to be provided with an illumination system 20 configured to irradiate the surface of the wafer 10 supported on the stage 5 with an illumination light as a parallel light; a light receiving system 30 configured to condense reflected light, diffracted light, and the like, from the wafer 10 receiving the irradiation of the illumination light; an imaging device 35 configured to detect an image of the surface of the wafer 10 receiving the light condensed by the light receiving system 30; an image processing section 40; a storing section (a memory section) 41; and a film-thickness calculator 50. The illumination system 20 is configured to include an illumination unit 21 configured to emit the illumination light; and an illumination-side concave mirror 25 configured to reflect the illumination light emitted from the illumination unit 21 toward the surface of the wafer 10. The illumination unit 21 is configured to include a light source 22 such as a metal halide lamp, a mercury lamp, and the like; a light adjusting section 23 configured to adjust light intensity by extracting the light having a predetermined wavelength from the lights from the light source 22; and a light guiding fiber 24 configured to guide the light from the light adjusting section 23 as the illumination light to the illumination-side concave mirror 25.

Then, the light from the light source 22 is passed through the light adjusting section 23, and the illumination light having a predetermined wavelength (248 nm, for example) is emitted from the light guiding fiber 24 toward the illumination-side concave mirror 25. Then, because the exit portion of the light guiding fiber 24 is arranged on the focal plane of the illumination-side concave mirror 25, the illumination light emitted from the light guiding fiber 24 to the illumination-side concave mirror 25 becomes a parallel light beam due to the illumination-side concave mirror 25 to irradiate the surface of the wafer 10 held on the stage 5. Further, it is possible to adjust the relation between the incident angle and the exit angle to the wafer 10 for the illumination light by tilting the stage 5 to change the angle of placing the wafer 10.

Figure 2:
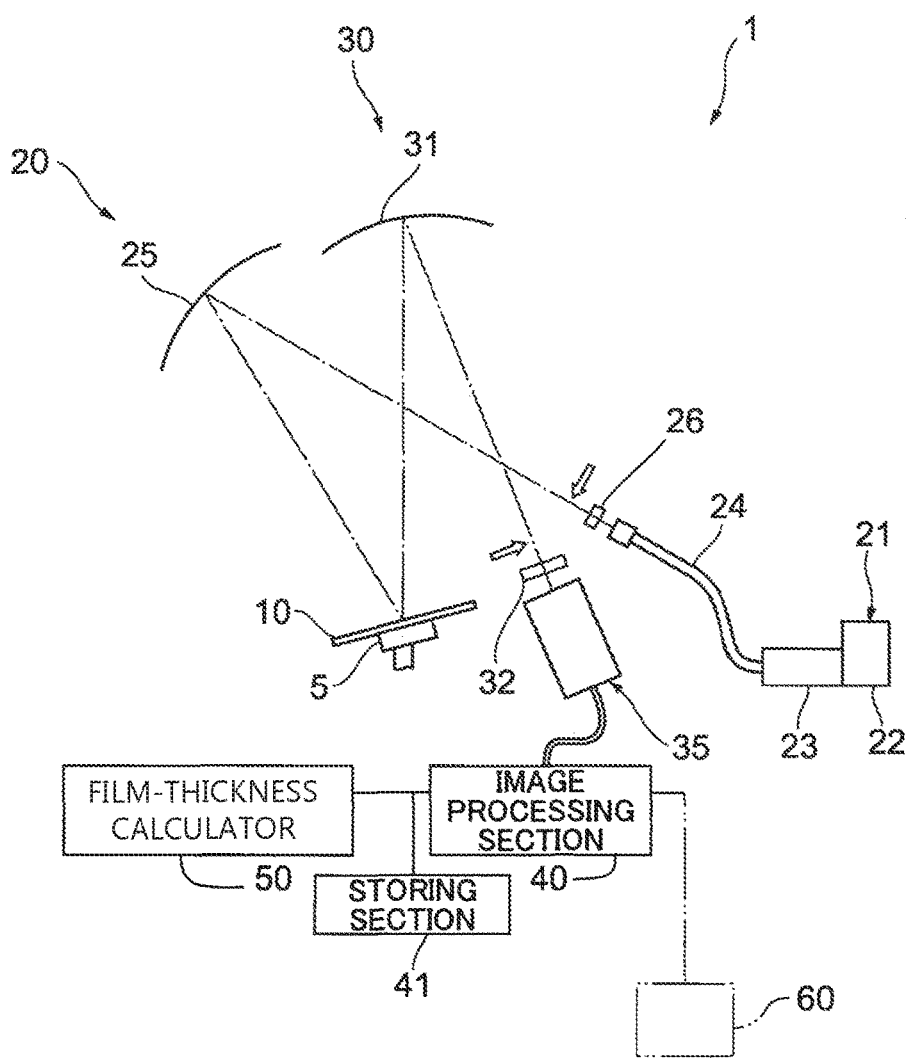
FIG. 2 shows a state of inserting a polarizing filter into an optical path of the surface inspection apparatus.

Further, between the light guiding fiber 24 and the illumination-side concave mirror 25, an illumination-side polarizing filter 26 is provided to be insertable into and removable from the optical path. As shown in FIG. 1, under a condition that the illumination-side polarizing filter 26 is removed from the optical path, inspection is carried out by utilizing diffracted light (to be referred to as diffraction inspection hereinbelow for convenience) and, as shown in FIG. 2, under a condition that the illumination-side polarizing filter 26 is inserted in the optical path, inspection is carried out by utilizing polarized light (by utilizing a change in polarization state due to form birefringence). This inspection will be referred to as PER inspection hereinbelow for convenience, and the illumination-side polarizing filter 26 will be described in detail hereinafter.

The light receiving system 30 condenses the exit light (diffracted or reflected light) from the surface of the wafer 10. The light receiving system 30 mainly includes a light-receiving-side concave mirror 31 provided to face the stage 5. The exit light condensed by the light-receiving-side concave mirror 31 (diffracted or reflected light) reaches the imaging plane of the imaging device 35 to form an image of the wafer 10.

Further, a light-receiving-side polarizing filter 32 is provided to be insertable into and removable from the optical path between the light-receiving-side concave mirror 31 and the imaging device 35. As shown in FIG. 1, under a condition that the light-receiving-side polarizing filter 32 is removed from the optical path, diffraction inspection is carried out. As shown in FIG. 2, under a condition that the light-receiving-side polarizing filter 32 is inserted in the optical path, the PER inspection is carried out (the light-receiving-side polarizing filter 32 will be described in detail hereinafter).

The imaging device 35 photoelectrical converts the surface image of the wafer 10 formed on the imaging plane to generate an image signal and output the image signal to the image processing section 40. The image processing section 40 generates a digital image of the wafer 10 based on the image signal of the wafer 10 inputted from the imaging device 35. An inner memory (not shown) of the image processing section 40 previously stores image data of non-defective wafers. After generating an image of the wafer 10 (digital image), the image processing section 40 compares the image data of the wafer 10 with the image data of nondefective wafers, and inspects whether or not there is any defect (abnormity) in the surface of the wafer 10. Then, the inspection result from the image processing section 40 and the image of the relevant wafer 10 are outputted and displayed on an image display device (not shown). Further, the image processing section 40 is configured to be capable of setting the focus condition or the dose amount (exposure amount) of the optical exposer 60 by utilizing data in relation to the optical exposer 60 stored in the storing section 41 (details will be described hereinafter).

Figure 3:
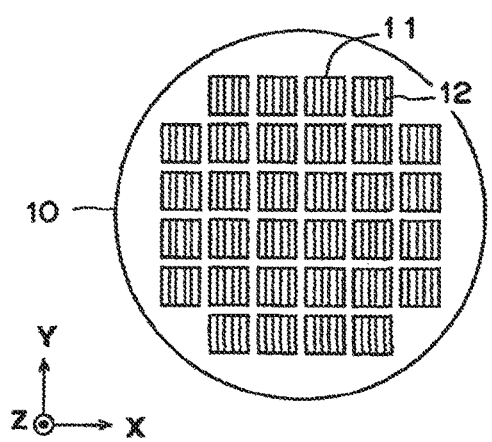
FIG. 3 is an external view of a surface of a semiconductor wafer.

By the way, the optical exposer 60 projects a predetermined mask pattern on the wafer 10 and exposes the uppermost resist film of the wafer 10. The wafer 10 is developed by a development device (not shown) and then carried onto the stage 5 by a carrier device (not shown) from a wafer cassette (not shown) or the development device. Further, at this time, the wafer 10 is carried onto the stage 5 in a state of being aligned with the pattern or the outer edge (notch, orientation flat or the like) of the wafer 10 as the reference. Further, on the surface of the wafer 10, as shown in FIG. 3, a plurality of chip regions 11 (shots) are arranged horizontally and vertically (in X and Y directions in FIG. 3), and in each chip region 11, a repetitive pattern 12 is formed as a semiconductor pattern such as a line pattern, a hole pattern, or the like. Detailed illustration is omitted. The optical exposer 60 is electrically connected to the surface inspection apparatus 1 of this embodiment via cables and the like.

Figure 12:
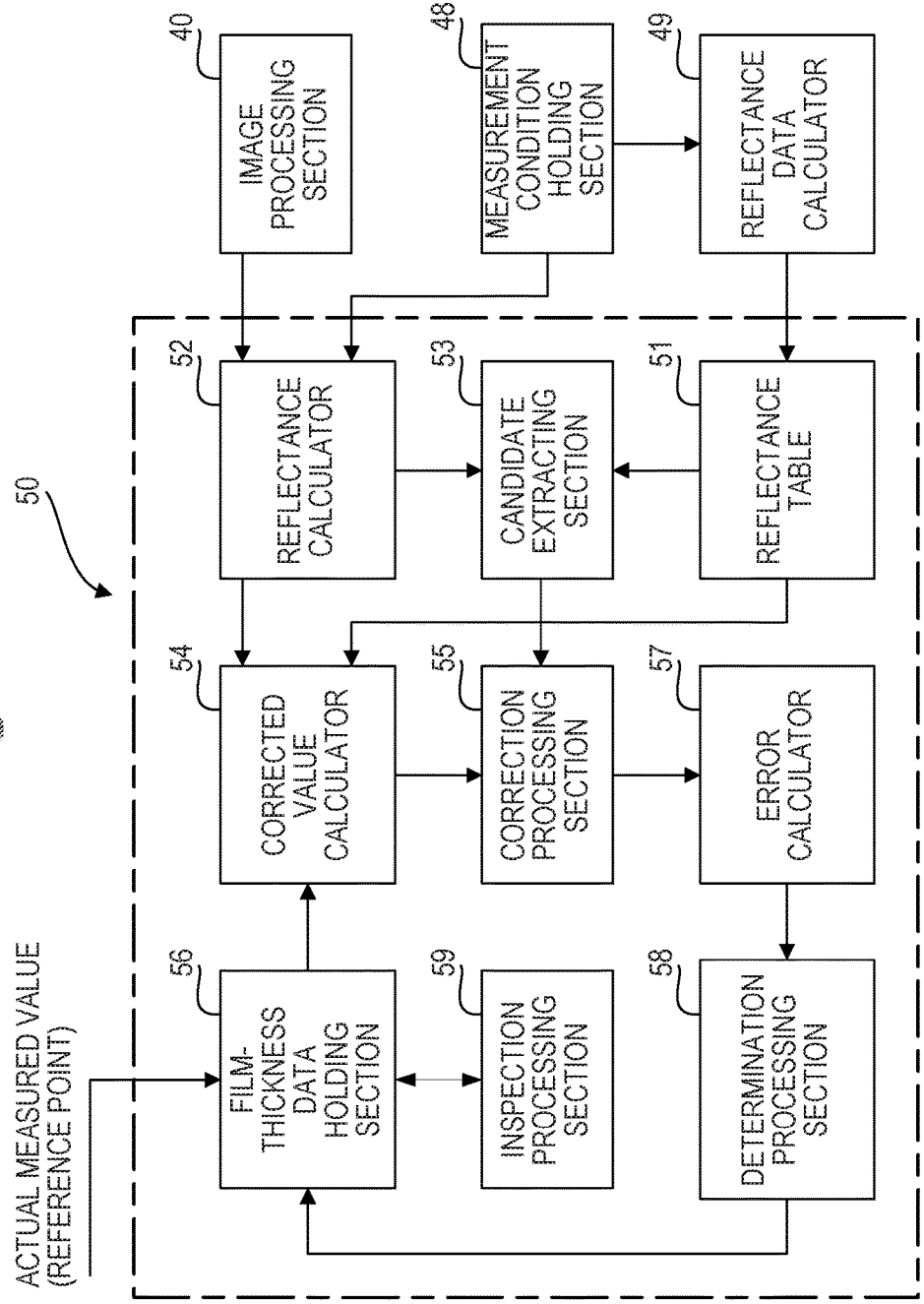
FIG. 12 is a block diagram showing a film-thickness calculator.

The film-thickness calculator 50 finds or obtains the film thickness of a thin film, such as the resist film and a silicon dioxide film, from the image data of the wafer 10 generated by the image processing section 40 (details will be described hereinafter). As shown in FIG. 12, the film-thickness calculator 50 is electrically connected to a measurement condition holding section 48 and a reflectance data calculator 49. There is stored, in the measurement condition holding section 48, measurement condition information including the incidence angle of the illumination light to the wafer 10, spectroscopic intensity (intensity for each wavelength) of the illumination light emitted from the illumination unit 21, and spectral sensitivity (sensitivity for each wavelength) of the imaging device 35 and complex refractive index for each wavelength of the base material (for example, Si) and the thin film of the wafer 10.

It is possible to specify, in advance, the complex refractive index for each wavelength of the base material of the wafer 10 and the complex refractive index for each wavelength of a substance forming the single-layered thin film formed on the base material of the wafer 10 by measuring at least one reference point (for example, a center position of the wafer 10) of the wafer 10, for example, by using a refractive index measurer utilizing ellipsometry. Then, based on the complex refractive index for each wavelength specified as described above and the incidence angle of illumination light to the wafer 10, the reflectance data calculator 49 can calculate the reflectance including interference of the reflected light from the surface and the back surface of the thin film, in a case that the thin films having various film thicknesses are each formed on the base material of the wafer 10 under an angle condition which is realized by the illumination system 20 as shown in FIG. 1.

Figure 13:
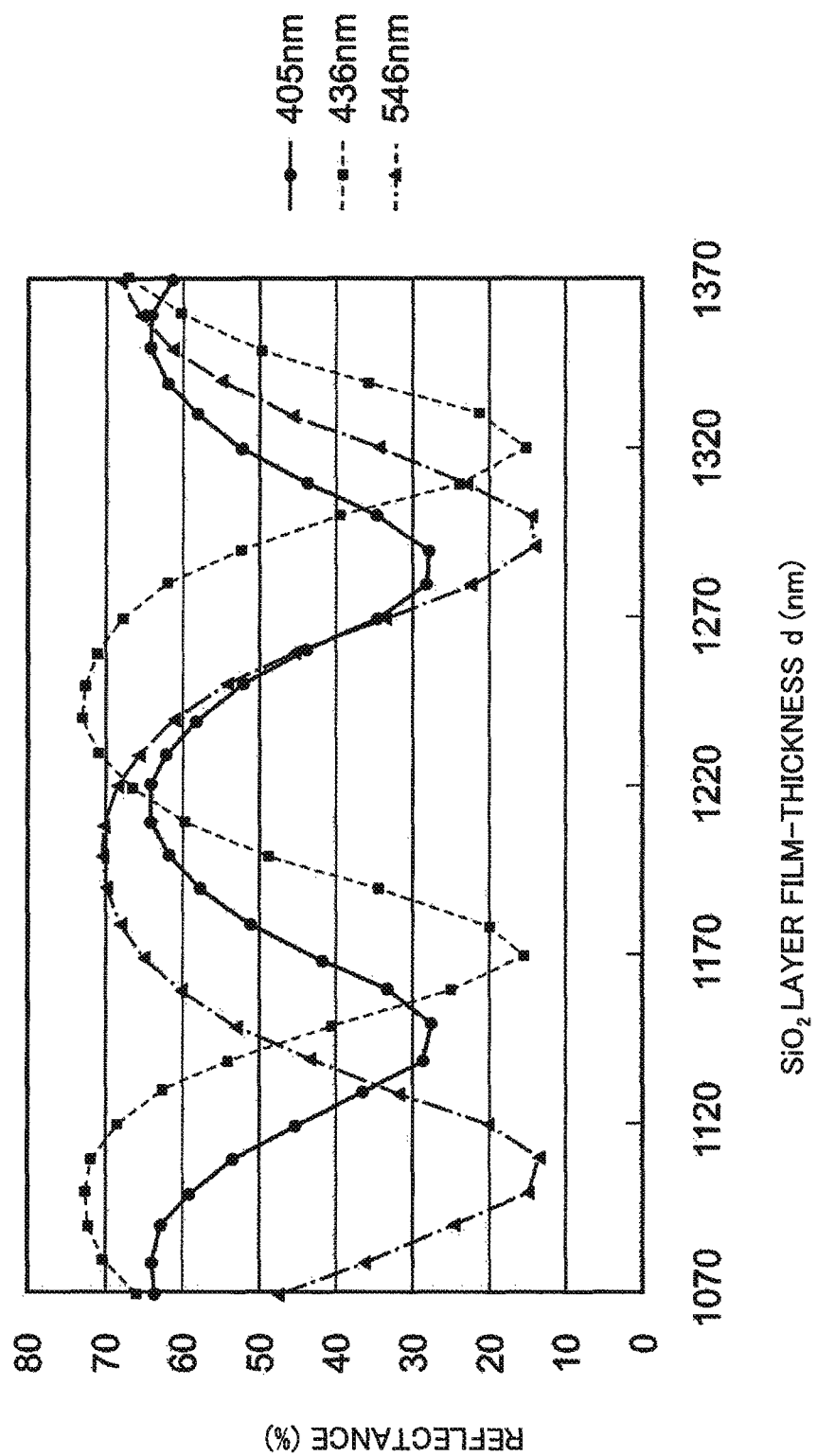
FIG. 13 shows a correspondence relation between a film thickness and reflectance of each wavelength.

For example, the following case is allowable. That is, the complex refractive index of the base material (for example, Si) of the wafer 10 and the complex refractive index of the material (for example, $SiO_2$) of the single-layered film are substituted in a formula used for thin-film interference corresponding to the angle condition as described above; and the reflectance is calculated within a range of the film thickness 1070 nm to 1370 nm, for example, in a case that the illumination light is supposed to be the wavelengths of h-ray (wavelength 405 nm), g-ray (436 nm), e-ray (546 nm), etc., while changing the film thickness every 10 nm. Then, the calculation result is retained in a reflectance table 51 of the film-thickness calculator 50. For example, with respect to the respective illumination lights having the wavelengths of 405 nm, 436 nm, and 546 nm, reflectance curves, each of which is obtained by calculating the reflectance from the thin film of silicon dioxide having each film thickness shown on the horizontal axis, are depicted by bold solid lines (405 nm), bold dashed lines (436 nm), and non-bold alternate long and short dash lines (546 nm) in FIG. 13.

Further, the following case is also allowable. That is, a geometric film thickness of the thin film on at least one reference point as described above is measured, for example, by a film-thickness measurement machine provided separately. Then, the measurement result(s) is/are retained in a film-thickness data holding section 56 and used for correction of the film-thickness measurement based on the reflectance.

In order to carry out the diffraction inspection of the surface of the wafer 10 by utilizing the surface inspection apparatus 1 configured in the above manner, first, the illumination-side polarizing filter 26 and the light-receiving-side polarizing filter 32 are removed from the optical path as shown in FIG. 1, and the wafer 10 is carried onto the stage 5 by the carrier device (not shown). Further, it is possible to place the wafer 10 on the stage 5 in predetermined position and direction since an alignment mechanism (not shown) acquires positional information of the pattern (notch, orientation flat, or alignment mark) formed on the surface of the wafer 10 in carrying.

Next, the stage 5 is rotated such that the direction of illuminating the surface of the wafer 10 coincides with the repetitive direction of the pattern (in the case of a line pattern, the illumination direction is perpendicular to the line). Further, the stage 5 is set (tilted) to satisfy the following equation (Eq. 1) by Huygens' principle, where "P" represents the pattern pitch, "λ" represents the wavelength of the illumination light irradiating the surface of the wafer 10, "θ1" represents the incidence angle of the illumination light, and "θ2" represents the exit angle of the nth-order diffracted light.

$$P = n \times \lambda / \{\sin(\theta 1) - \sin(\theta 2)\} \quad \text{(Eq. 1)}$$

Next, the illumination system 20 irradiates the surface of the wafer 10 with the illumination light. When irradiating the surface of the wafer 10 with the illumination light under such a condition, the light from the light source 22 in the illumination unit 21 is passed through the light adjusting section 23. The illumination light having a predetermined wavelength (for example, 248 nm or emission-line spectrum of mercury) exits from the light guiding fiber 24 to the illumination-side concave mirror 25, and the illumination light reflected by the illumination-side concave mirror 25 becomes a parallel light beam to irradiate the surface of the wafer 10. The diffracted light diffracted by the surface of the wafer 10 is condensed by the light-receiving-side concave mirror 31, and reaches the imaging plane of the imaging device 35 to form a (diffraction) image of the wafer 10.

Here, the imaging device 35 photoelectrical converts the surface image of the wafer 10 formed on the imaging plane to generate an image signal, and outputs the image signal to the image processing section 40. The image processing section 40 generates a digital image of the wafer 10 based on the image signal of the wafer 10 inputted from the imaging device 35. Further, after generating the image (digital image) of the wafer 10, the image processing section 40 compares the image data of the wafer 10 with the image data of nondefective wafers to inspect whether or not there is any defect (abnormity) in the surface of the wafer 10. Then, the inspection result from the image processing section 40 and the image of the relevant wafer 10 are outputted and displayed on the image display device (not shown).

Figure 6:
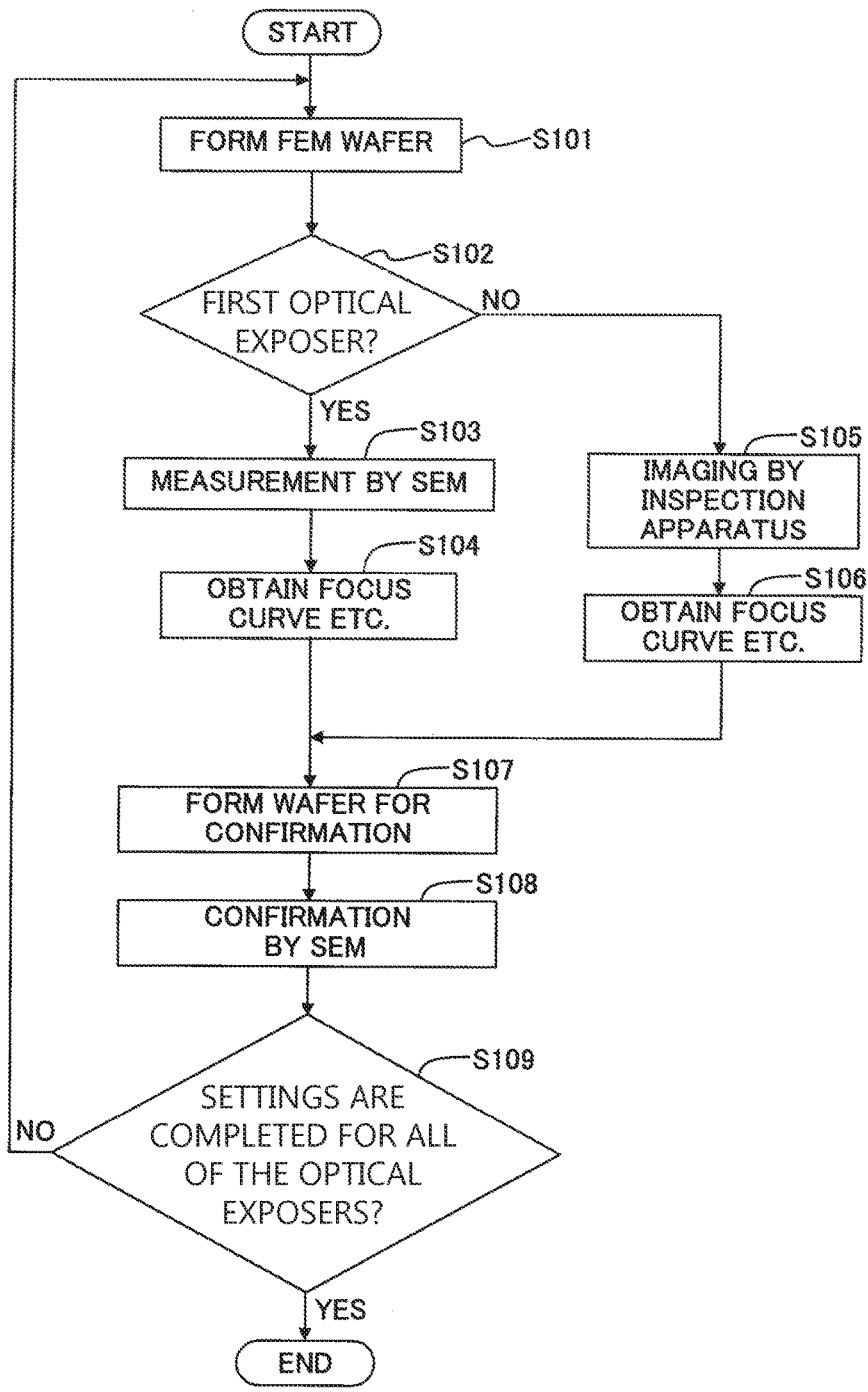
FIG. 6 is a flowchart showing a method for performing setting with respect to the same process for a plurality of optical exposers.
Figure 8:
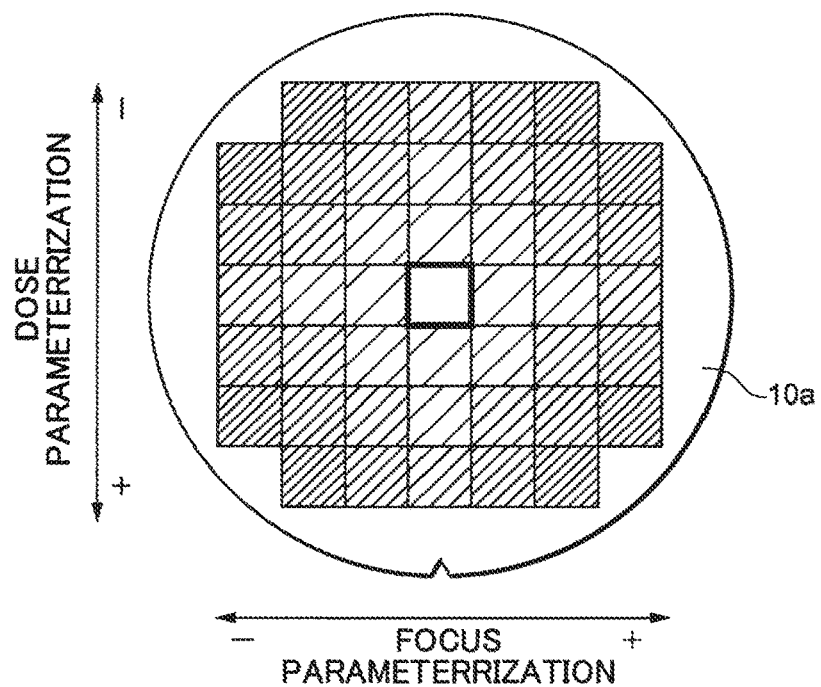
FIG. 8 shows an example of a FEM wafer.

Further, in a case that the same pattern is formed by performing exposure using each of the plurality of optical exposers and that the dose amount (exposure amount) and/or the focus condition is/are varied from each of the optimal states in each of the optical exposers, the profile of the pattern formed by performing the exposure using each of the optical exposers is more likely to change in accordance with each of the variations. Thus, in a case that the setting with respect to the same pattern is performed for each of the optical exposers 60, the image processing section 40 is capable of performing the settings of the focus condition and dose amount for each of the optical exposers 60 subsequent to a second optical exposer by using data of the focus condition and dose amount (exposure amount) set in a first optical exposer 60. Here, an explanation will be made about a method for performing setting with respect to the same process for the plurality of optical exposers 60 with reference to a flowchart shown in FIG. 6. At first, as shown in FIG. 8, it is formed a wafer (hereinafter, referred to as a FEM wafer 10a) in which a repetitive pattern (in this embodiment, the repetitive pattern is supposed to be a line pattern) is formed while changing the focus and the dose amount of the optical exposer 60 for each exposure shot in a stepwise manner in accordance with each of the preset values (step S101). In this situation, the exposure is performed while changing the focus and the dose amount in a matrix state for each exposure shot and the development is performed. Noted that the central thick-frame in FIG. 8 corresponds to a reference shot (for example, the shot exposed by the optimal focus condition and dose amount in terms of design); and the variations of the focus condition and dose amount for each shot with respect to the reference shot are expressed by shading of hatching.

After forming the FEM wafer 10a, in a case that the settings are performed for the first optical exposer 60 (step S102: YES), the line width of the line pattern which is formed on the surface of the FEM wafer 10a by the first optical exposer 60 is measured by using an electron microscope (CD-SEM) for each of the five spots in one exposure shot; and the measurement is performed for all of the exposure shots (step S103). As the measurement spot of the line width, it is possible to select the spot at which the profile (line width) of the pattern is changed depending on the changes of the focus and dose amount. Further, as needed, it is possible to select the spot at which the profile (line width) of the pattern is changed in response only to the change of the focus; or it is possible to select the spot at which the profile (line width) of the pattern is changed in response only to the change of the dose amount.

After measuring the line width of the line pattern by using the electron microscope (CD-SEM), it is manually found a graph (line-width reference focus curve) showing change of the line width (vertical axis) with respect to change of the focus (horizontal axis) for each of the five measurement spots in the exposure shot (step S104). In this situation, the line-width reference focus curve is found so that each line width (or roughness) depending on the change of the focus is measured in the same dose amount (best dose amount is desired). In a case that the wafer, in which the shot with the same focus and dose amount is performed a plurality of times, is used, a plurality of line widths (or roughnesses) are measured for the plurality of shots with the same focus and dose amount; and the line-width reference focus curve is found by using an average value of the measured line widths (or roughnesses). After finding the line-width reference focus curve, a focus value having a maximum line width (in a case of the roughness, a focus value having a minimum roughness) is defined as the best focus; and the focus value having the maximum line width in the line-width reference focus curve is found as the optimal focus condition (best focus) of the optical exposer 60. Accordingly, it is possible to set the optimal focus condition for each of the five spots in the exposure shot in the first optical exposer 60. As for the line-width reference focus curve, it is possible to find the graph and the optimal focus condition by sending the data to a computer (not shown) from the electron microscope (CD-SEM) and performing the least-squares method etc.

After measuring the line width of the line pattern by using the electron microscope (CD-SEM), it is manually found a graph (line-width reference dose curve) showing change of the line width (vertical axis) with respect to change of the dose amount (horizontal axis) for each of the five measurement spots in the exposure shot. In this situation, the line-width reference dose curve is found so that each line width depending on the change of the dose amount is measured in the same focus (best focus is desired). In a case that the wafer, in which the shot with the same focus and dose amount is performed a plurality of times, is used, a plurality of line widths are measured for the plurality of shots with the same focus and dose amount; and the line-width reference dose curve is found by using an average value of the measured line widths. After finding the line-width reference dose curve, a dose amount in which the line width of a design value is obtained in the line-width reference dose curve is found as the optimal dose amount (best dose amount) of the optical exposer 60. Accordingly, it is possible to set the optimal dose amount for each of the five spots in the exposure shot in the first optical exposer 60. The focus condition and the dose amount obtained as described above are, for example, manually inputted to the first optical exposer 60. As for the line-width reference dose curve, it is possible to find the graph and the optimal dose amount by sending the data to a computer (not shown) from the electron microscope (CD-SEM) and performing the least-squares method etc., in a similar manner as the line-width reference focus curve. Further, it is possible to input the optimal focus condition and the optimal dose amount to the optical exposer 60 by using communication method (cable or radio).

In a case that the settings are performed for each of the optical exposers 60 subsequent to the second optical exposer among the plurality of the optical exposers 60 (S102: NO), an image of an entire surface of the FEM wafer 10a, in which the line pattern is formed by each of the optical exposers 60 subsequent to the second optical exposer, is taken (step S105). Here, in a similar manner as in the case of the diffraction inspection, the FEM wafer 10a is carried onto the stage 5; the illumination system 20 irradiates the surface of the FEM wafer 10a with the illumination light; and the imaging device 35 photoelectrical converts the diffraction image of the FEM wafer 10a to generate the image signal and output the image signal to the image processing section 40. Further, in this situation, the diffraction condition of the FEM wafer 10a is found by utilizing information of the exposed mask pattern or diffraction condition search (to measure the intensity of the diffracted light by tilting the stage 5 in an angular range other than specular condition) to perform the settings in a similar manner as in the case of the diffraction inspection to obtain the diffracted light. The diffraction condition search refers to the function of changing the tilt angle of the stage 5 in a non-specular angular range in a stepwise manner and acquiring an image at each tilt angle to find the tilt angle for a brighter image, that is, the diffracted light is obtainable. An azimuth of the FEM wafer 10a (posture of the exposed pattern with respect to the illumination direction of the illumination light) is arranged so that the repetitive direction of the exposed pattern (in the case of the line pattern, the direction is perpendicular to the line) coincides with the illumination direction.

After the focus condition and the dose amount are set to be the optimal states in the first optical exposer 60, in a similar manner as in the case of the diffraction inspection, the image of the entire surface of the FEM wafer 10a, in which the line pattern is formed by the first optical exposer 60 set in the optimal state, is taken in advance by using the surface inspection apparatus 1 of this embodiment. After taking the image of the entire surface of the FEM wafer 10a in which the line pattern is formed by the first optical exposer 60, the image processing section 40 of the surface inspection apparatus 1 finds, for each of the five measurement spots in the exposure shot, the graph (hereinbelow, referred to as a reference focus curve) showing change of luminance (signal intensity) of the diffracted light from the line pattern (vertical axis) with respect to change of the focus in an appropriate dose amount (horizontal axis); and stores the graph in the storing section 41. In this situation, it is measured, for each of the five measurement spots, the luminance (signal intensity) of the diffracted light from the line pattern depending on the change of the focus under the appropriate focus condition and each of the dose amounts; a relation between the change of the dose amount and the change of the luminance is found; and the relation is stored in the storing section 41.

After taking the image of the entire surface of the FEM wafer 10a in which the line pattern is formed by each of the optical exposers 60 subsequent to the second optical exposer, the image processing section 40 finds, for each of the five measurement spots in the exposure shot, the graph (hereinbelow, referred to as a sample focus curve) showing change of the luminance (signal intensity) of the diffracted light from the line pattern (vertical axis) with respect to change of the focus (horizontal axis) (step S106). In this situation, it is measured the luminance (signal intensity) of each of the plurality of diffracted lights from the line pattern depending on the change of the focus in the same dose amount (best dose amount); the sample focus curve is found by using an average value of the measured luminance (signal intensity) of the diffracted lights.

Figure 9B:
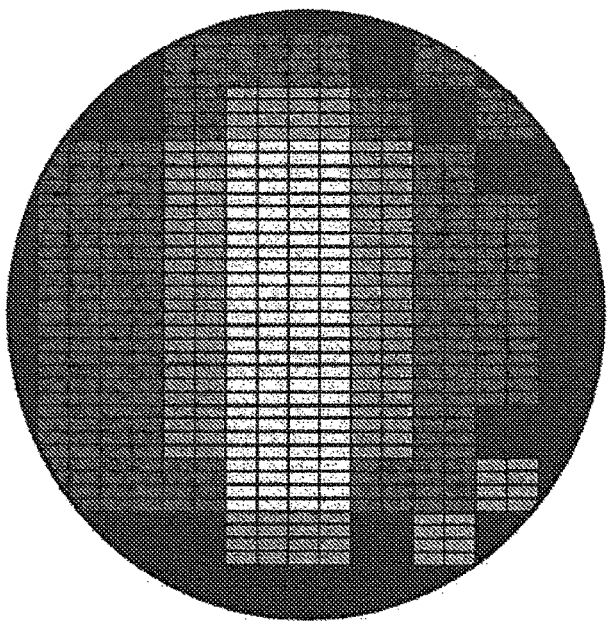
FIGS. 9A and 9B are diagrams in which wafers exposed by different optical exposers under the same condition are compared.
Figure 9A:
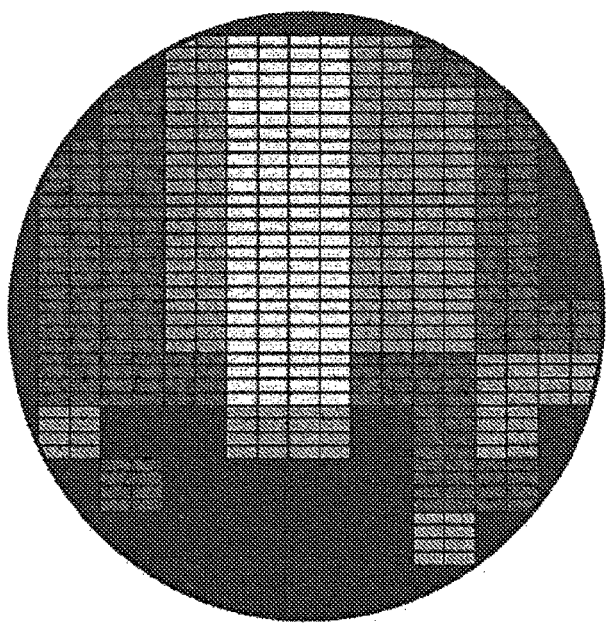

In a case that each of the FEM wafers 10a is formed by one of the same type of optical exposers 60 under the same settings, the profile of the line pattern formed on the surface of the FEM wafer 10a differs in each device (that is, the luminance (signal intensity) of the diffracted light from the line pattern differs in each device), as shown in FIGS. 9A and 9B while being compared with each other. In a case that the image of the entire surface of the FEM wafer 10a is taken by the surface inspection apparatus 1 of this embodiment, the line patterns formed by the same type of optical exposers 60 are different from one another such that change of state of each of the patterns depending on changes of the focus and dose amount is generated in the form of offset horizontally and vertically (in a case of FIG. 9B, offset rightward with respect to FIG. 9A). This difference corresponds to changes of the focus and dose amount in each of the optical exposers 60 subsequent to the second optical exposer with respect to the first optical exposer 60. Thus, when the settings are performed while correcting the changes, it is possible to set the appropriate focus condition and dose amount for each of the optical exposers 60 subsequent to the second optical exposer by utilizing the data of the focus condition and dose amount set in the first optical exposer 60.

Figure 10:
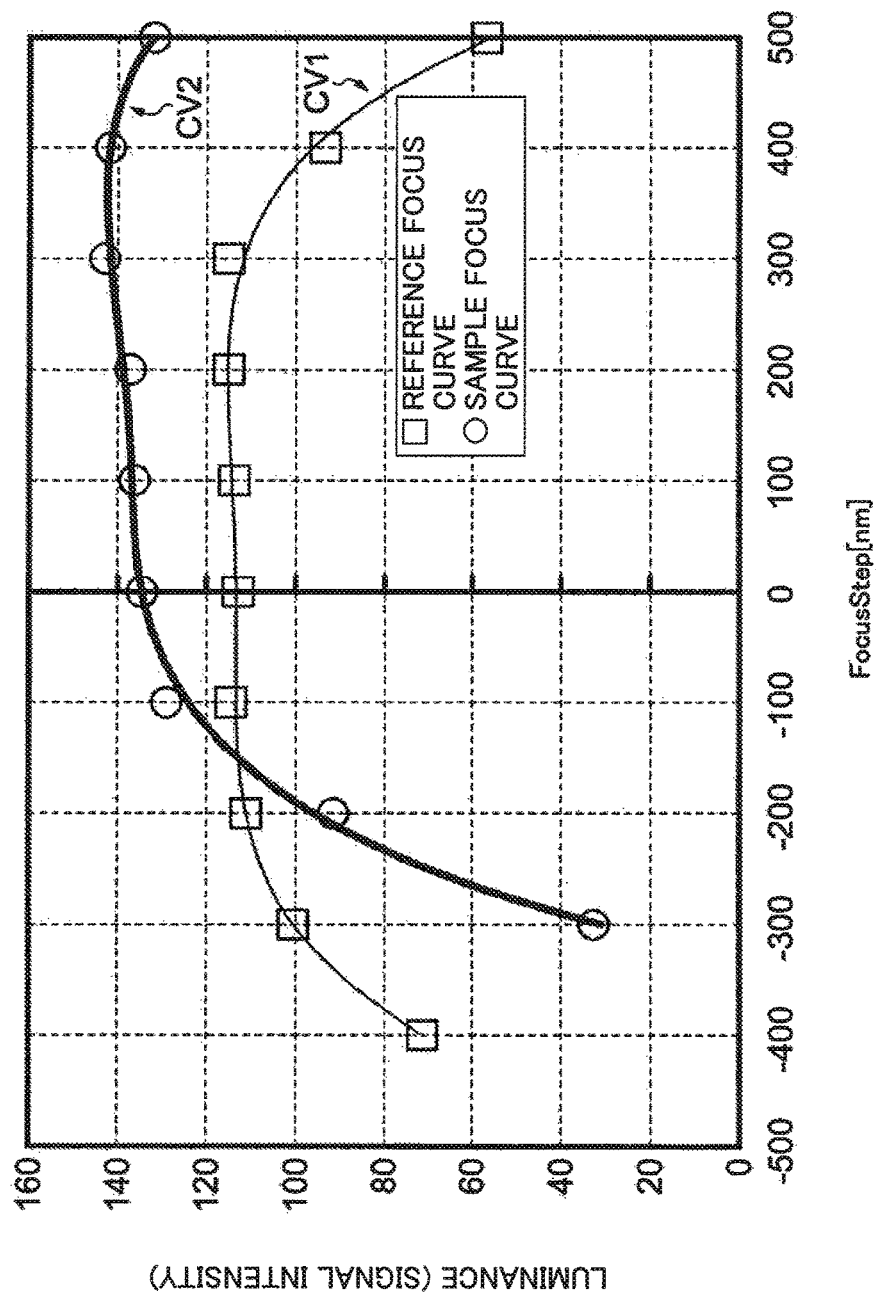
FIG. 10 shows an example of a reference focus curve and a sample focus curve.

Then, the image processing section 40 of the surface inspection apparatus 1 compares the reference focus curve stored in the storing section 41 and the sample focus curve to set the optimal focus condition and dose amount for each of the optical exposers 60 subsequent to the second optical exposer. FIG. 10 shows an example of a reference focus curve CV1 and an example of a sample focus curve CV2. It is possible to utilize, for example, a fourth-order function for the fitted curve of each of the reference focus curve CV1 and the sample focus curve CV2. As for the difference between the reference focus curve CV1 and the sample focus curve CV2 generated in the same type of the optical exposers 60, the difference in the direction of the horizontal axis is caused by the change of the focus; and the difference in the direction of the vertical axis is caused by the change of the dose amount. The reason thereof is as follows. That is, although the luminance (signal intensity) changes in accordance with the change of the dose amount, the tendency between the focus and the luminance change do not change other than movement of the focus curve in the luminance direction.

Figure 11:
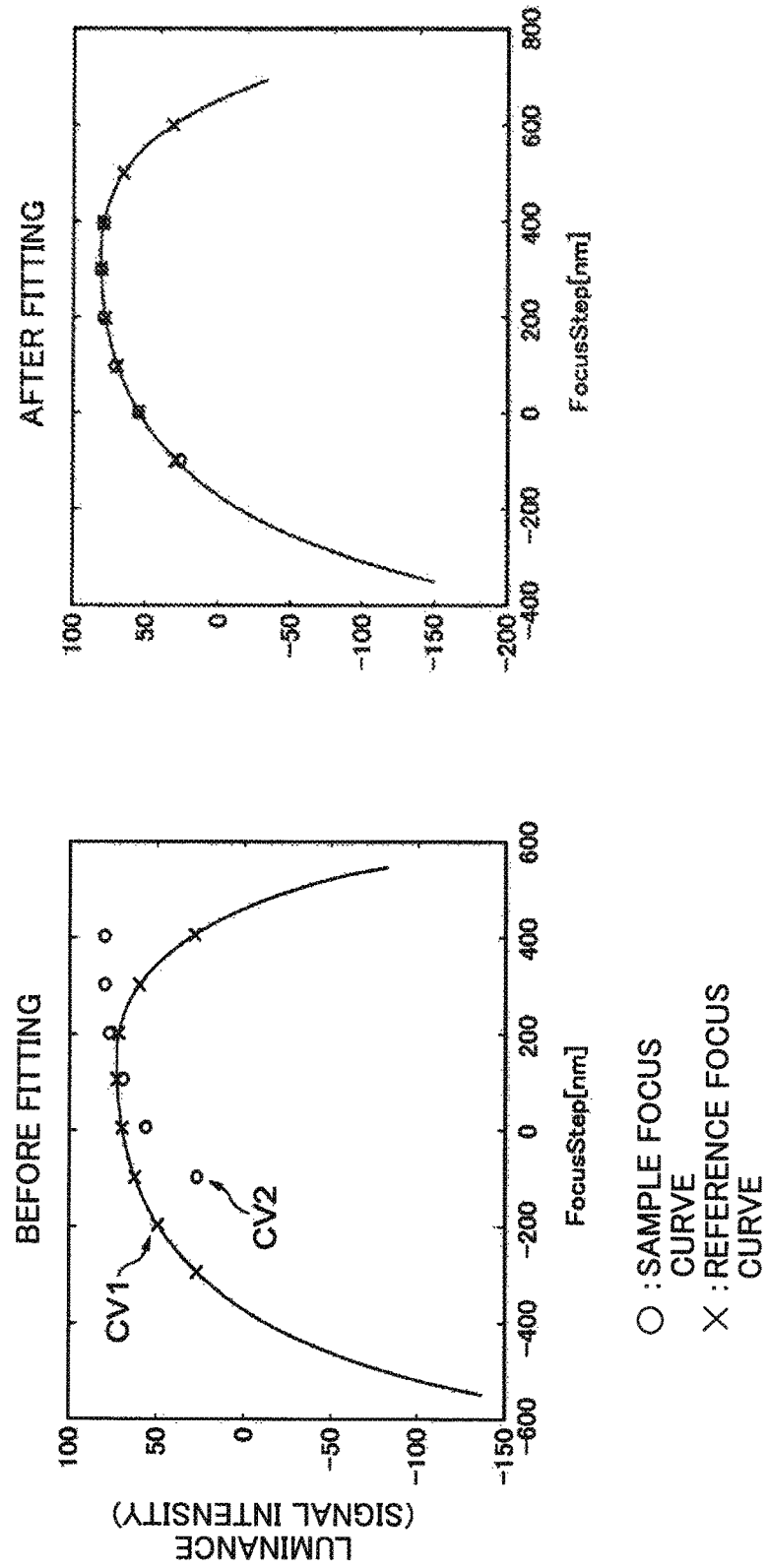
FIG. 11 shows a state in which the reference focus curve is fitted to the sample focus curve.

In this situation, at first, the image processing section 40 fits the reference focus curve CV1 to the sample focus curve CV2 to have the best correlation by using an image process of a pattern matching as shown in FIG. 11. A specific example of the pattern matching includes a technique as follows. That is, the reference focus curve CV1 and the sample focus curve CV2 are approximated by a predetermined function (for example, the fourth-order function); the function approximating the sample focus curve CV2 is moved in the direction of the horizontal axis in a state that the function approximating the reference focus curve CV1 is fixed; and a position, at which the sum of the square of the difference between both of the functions in the direction of the vertical axis is smallest, is determined as a position having the best correlation. In FIG. 11, the illustration of the fitted curve of the sample focus curve CV2 is omitted. Next, the image processing section 40 finds respective moving amounts in the directions of the horizontal axis and the vertical axis generated when the reference focus curve CV1 is fitted to the sample focus curve CV2. This moving amount in the direction of the horizontal axis corresponds to the change of the focus of each of the optical exposers 60 (to be subjected to the setting) subsequent to the second optical exposer with respect to the first optical exposer 60; and the moving amount in the direction of the vertical axis corresponds to a luminance value caused by the change of the dose amount.

Then, the image processing section 40 finds the focus condition, in which the moving amount (change of the focus) in the direction of the horizontal axis of the reference focus curve CV1 is added to the focus condition set for each of the optical exposers 60 subsequent to the second optical exposer, as the optimal focus condition (best focus) of each of the optical exposers 60 (to be subjected to the setting) subsequent to the second optical exposer. That is, the moving amount in the direction of the horizontal axis generated when the sample focus curve CV2 is moved to be substantially coincident with the reference focus curve CV1 obtained in the first optical exposer is found as the change with respect to the optimal state of the focus condition of each of the optical exposers 60 subsequent to the second optical exposer. Similarly, the image processing section 40 finds the dose amount, in which the moving amount (change of the dose amount) in the direction of the vertical axis of the reference focus curve CV1 is added to the dose amount set for the first optical exposer 60, as the optimal dose amount (best dose amount) of each of the optical exposers 60 (to be subjected to the setting) subsequent to the second optical exposer. The correlation between the change of the dose amount and the change of the luminance is preferably found in advance.

Accordingly, the image of the FEM wafer 10a is taken by using the surface inspection apparatus 1 of this embodiment and the optimal focus condition and dose amount for each of the optical exposers 60 subsequent to the second optical exposer is found automatically by the image processing section 40, and thus there is no need to measure the line width of the line pattern by using the electron microscope (CD-SEM). Therefore, it is possible to set the optimal focus condition and dose amount for each of the five spots in the exposure shot for each of the optical exposers 60 subsequent to the second optical exposer in a short period of time. The focus condition and dose amount obtained as described above are, for example, outputted from the image processing section 40 to each of the optical exposers 60 (to be subjected to the setting) subsequent to the second optical exposer.

It is allowable to form a plurality of FEM wafers to find focus curves, respectively. In this case, the matrix of each of the FEM wafers is preferably set to cancel out the effect of the condition(s) other than the focus condition (or dose amount).

Further, in the case that the optimal focus condition and dose amount are set for each of the optical exposers 60 subsequent to the second optical exposer and that the film thickness (height of the pattern after the development) of the resist film of the FEM wafer 10a is varied, the correlation relation of the luminance (signal intensity) in the image of the FEM wafer 10a is not changed, but the luminance (signal intensity) is changed as a whole. That is, in a case that the film thickness of the resist film of the FEM wafer 10a is varied, the reference focus curve CV1 and the sample focus curve CV2 are each varied in the direction of the vertical axis (that is, the luminance value caused by the change of the dose amount is varied).

In view of the above, the following processes are preferably performed. That is, in the step S101, the film thickness of the resist film of each of the wafers to be exposed as the FEM wafer 10a is measured in advance (details will be described hereinafter) by using the surface inspection apparatus 1 of this embodiment before the exposure by the optical exposer 60 is performed; and in the step S106, in the case that the optimal focus condition and dose amount are set for each of the optical exposers 60 subsequent to the second optical exposer, the image processing section 40 performs the corrections of the focus condition and dose amount by using the film-thickness data of the wafer to be subjected to the settings inputted from the film-thickness calculator 50. In particular, the luminance (vertical axis) of the sample focus curve CV2 is corrected depending on the variation, of the film thickness of the wafer exposed by each of the optical exposers 60 subsequent to the second optical exposer, with respect to the film thickness of the wafer exposed by the first optical exposer 60. This corrects the variation of the luminance (signal intensity) due to the variation of the film thickness, and thus it is possible to set the optimal focus condition and dose amount with a high degree of accuracy. The correlation between the variation of the film thickness and the variation of the luminance (signal intensity) can be found in advance.

After setting the optimal focus condition and dose amount as described above, a wafer for confirmation (not shown), in which the line pattern (repetitive pattern) is formed by the optical exposer 60 having the settings of the optimal focus condition and dose amount, is formed (step S107). In this situation, the exposure is performed in the best focus state and the best dose amount for all of the exposure shots and then the development is performed.

After forming the wafer for confirmation (not shown), the line width of the line pattern etc., formed in the surface of the wafer for confirmation (not shown) is measured by using the electron microscope (CD-SEM) and it is confirmed as to whether or not the set focus condition and the set dose amount are appropriate (step S108). It is possible to select a portion at which the profile (line width) of the pattern is changed depending on the changes of the focus and dose amount as a portion at which the line width is measured.

After completing the confirmation by the electron microscope (CD-SEM), in a case that the settings of the focus condition and dose amount are not completed for all of the optical exposers 60 (step S109: No), the process returns to the step S101. In a case that the settings of the focus condition and dose amount are completed for all of the optical exposers 60 (step S109: Yes), the settings of the focus condition and dose amount are completed.

Figure 7:
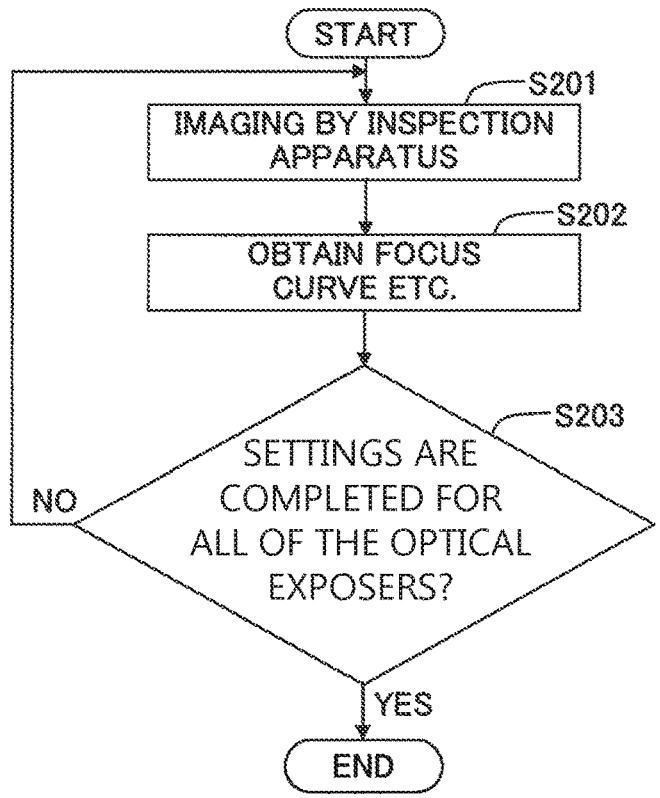
FIG. 7 is a flowchart showing a method for finding variation states of a focus and a dose amount for a plurality of optical exposers.

Further, the image processing section 40 is capable of periodically finding the variation states of the focus and dose amount in the optical exposer 60 by using the data of the reference focus curve stored in the storing section 41. An explanation will be made about a method for periodically measuring the variation states of the focus and dose amount in each of the optical exposers 60 with reference to the flowchart shown in FIG. 7. At first, the FEM wafer 10a is formed by the optical exposer 60 in which the settings have been performed as described above and the image of the entire surface of the FEM wafer 10a is taken by using the surface inspection apparatus 1 of this embodiment in a similar manner as in the case of the diffraction inspection (step S201).

After taking the image of the entire surface of the FEM wafer 10a in which the line pattern is formed by the optical exposer 60 in which the settings have been performed as described above, the image processing section 40 finds, for each of the five measurement spots in the exposure shot, the graph (hereinafter referred to as a condition focus curve) showing change of the luminance (signal intensity) of the diffracted light from the line pattern (vertical axis) with respect to change of the focus (horizontal axis) (step S202). In this situation, the luminance (signal intensity) of each of the diffracted lights from the line pattern depending on the change of the focus in the same dose amount (best dose amount) is measured; and the condition focus curve is found by using an average value of the measured luminance (signal intensity) of the diffracted lights.

In a case that each of the FEM wafers 10a is formed by each of the optical exposers 60 after the focus condition and the dose amount are set as described above, it is not likely to cause the difference in each line pattern formed in the surface of the FEM wafer 10a by each of the optical exposers 60 in normal cases. However, in a case that the state of the optical exposer 60 is changed for some reasons, the focus condition and the dose amount are varied in this optical exposer 60; and the state of the line pattern formed in the surface of the FEM wafer 10a is changed. After taking the image of the entire surface of the FEM wafer 10a by the surface inspection apparatus 1 of this embodiment, in a case that the state of the optical exposer 60 is changed for some reasons, the change of the state of the pattern depending on the changes of the focus and dose amount is generated in the form of the offset horizontally and vertically. Thus, by finding the changes of the focus and dose amount utilizing the reference focus curve used in the previous settings, it is possible to find the variation states of the focus and dose amount in the optical exposer 60.

The image processing section 40 compares the reference focus curve stored in the storing section 41 and the condition focus curve to find the variation states of the focus and dose amount in the optical exposer 60. Detailed illustration being omitted, it is possible to utilize, for example, the fourth-order function for the fitted curve of the condition focus curve. In a case that it is caused the difference between the reference focus curve and the condition focus curve, the difference in the direction of the horizontal axis is caused by the change of the focus; and the difference in the direction of the vertical axis is caused by the change of the dose amount.

At first, the image processing section 40 fits the reference focus curve to the condition focus curve to have the best correlation by using the image process of the pattern matching. Next, the image processing section 40 finds respective moving amounts in the directions of the horizontal axis and the vertical axis generated when the reference focus curve is fitted to the condition focus curve. This moving amount in the direction of the horizontal axis corresponds to the change of the focus of the optical exposer 60 depending on the change in the state of the optical exposer 60; and the moving amount in the direction of the vertical axis corresponds to the luminance value caused by the change of the dose amount.

The image processing section 40 finds the variation amount of the focus from the moving amount of the reference focus curve in the direction of the horizontal axis; and finds the variation amount of the dose amount from the moving amount of the reference focus curve in the direction of the vertical axis. By doing so, the image of the FEM wafer 10a is taken by using the surface inspection apparatus 1 of this embodiment and the variation states of the focus and dose amount in the optical exposer 60 are found automatically by the image processing section 40, and thus there is no need to measure the line width of the line pattern etc., by using the electron microscope (CD-SEM). Therefore, it is possible to measure the variation states of the focus and dose amount for each of the optical exposers 60 in a short period of time. Since it is possible to use the reference focus curve CV1 found in the first measurement in each of the measurements subsequent to the second measurement, there is no need to measure the pattern exposed by the first optical exposer by using the electron microscope (CD-SEM).

After finding the variation amounts of the focus and dose amount, in a case that the measurements are not completed for all of the optical exposers 60 (step S203: No), the process returns to the step S201. In a case that the measurements are completed for all of the optical exposers 60 (step S203: Yes), the measurements of the variation states of the focus and dose amount for each of the optical exposers 60 are completed.

Further, the following processes can be performed. That is, in the step S201, the film thickness of the resist film of each of the wafers to be exposed as the FEM wafer 10a is measured in advance (details will be described hereinafter) by using the surface inspection apparatus 1 of this embodiment before the exposure by the optical exposer 60 is performed; and in the step S202, in the case that the variation states of the focus and dose amount for each of the optical exposers 60 are measured, the image processing section 40 performs the corrections of the focus and dose amount by using the film-thickness data of the wafer to be subjected to the measurements inputted from the film-thickness calculator 50. In particular, the luminance of the condition focus curve (vertical axis) is corrected depending on the variation, of the film thickness of the wafer at the time of measuring the state, with respect to the film thickness of the wafer at the time of the setting. This corrects the variation of the luminance (signal intensity) due to the variation of the film thickness, and thus it is possible to measure the variation states of the focus and dose amount for each of the optical exposers 60 with a high degree of accuracy.

Here, an explanation will be made about a case in which the film thickness of the thin film (resist film) formed in the surface of the wafer (not shown) to be exposed is measured by using the surface inspection apparatus 1 of this embodiment. In this case, at first, the wafer to be exposed is transported on the stage 5 in a similar manner as in the case of the diffraction inspection. Next, the stage 5 is tilted so that the specular light of the illumination light reflected by the wafer surface can be received by the light receiving system 30.

Next, the illumination lights, each of which has one of five types of illumination wavelengths (for example, 546 nm, 436 nm, 405 nm, 313 nm, and 248 nm), irradiate the surface of the wafer, respectively. Here, the illumination light having one of the five types of wavelengths becomes the parallel light beam to irradiate the surface of the wafer. The specular light from the surface of the wafer is condensed by the light-receiving-side concave mirror 31, and reaches the imaging plane of the imaging device 35 to form the image (specular image) of the wafer to be exposed. Here, the imaging device 35 photoelectrical converts the image of the wafer formed on the imaging plane to generate an image signal, and outputs the image signal to the image processing section 40 for each of the five types of illumination wavelengths. The image processing section 40 generates a digital image of the wafer to be exposed based on the image signal inputted from the imaging device 35, and outputs the digital image to the film-thickness calculator 50.

An explanation will be made about a fitting calculation process executed by the film-thickness calculator 50. As for an optical system, which is telecentric both on the illumination and imaging sides, like the optical system in this embodiment, it is possible to adopt the thin-film interference expression in which the angle condition used for calculating the reflectance curve as described above is adopted for the entire area of the reflection image of the wafer to be subjected to the imaging. Therefore, it is possible to find the film thickness for each position on the wafer included in the reflection image by performing the fitting process in which it is searched, based on the reflectance table 51, the film thickness which provides combination of the reflectance indicated by the gradation value of each pixel included in the reflection image for each of the wavelengths inputted into the film-thickness calculator 50. The fitting calculation process will be described below.

Figure 14:
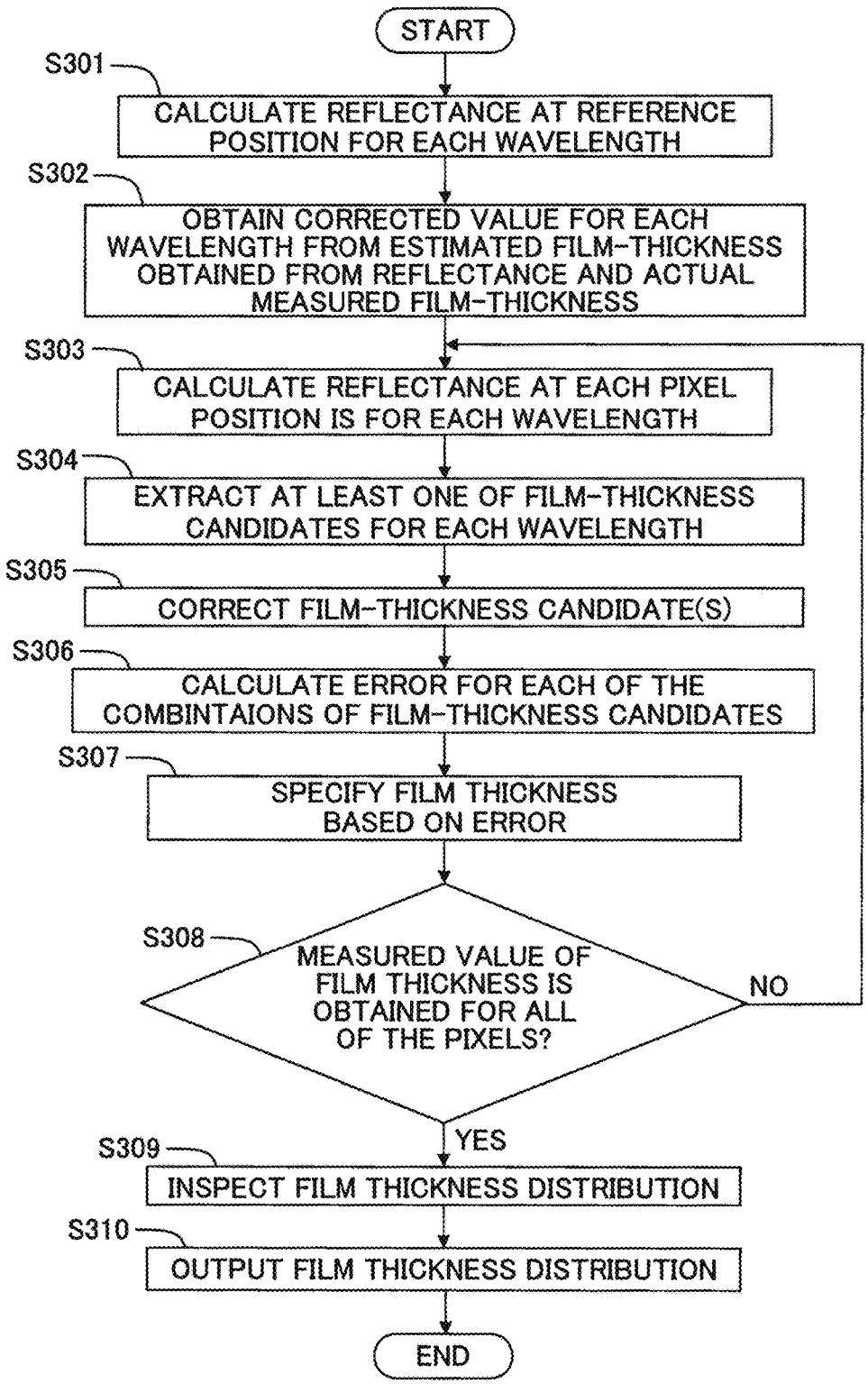
FIG. 14 is a flowchart showing a fitting calculation process.

FIG. 14 is a flowchart showing the fitting calculation process. At first, a reflectance calculator 52 calculates the reflectance $(R(\lambda 1), R(\lambda 2), \ldots)$ at a reference position for the wavelength $\lambda 1$, $\lambda 2$, of the illumination light selected when the reflection image is taken, based on the gradation value of the pixel at the reference position included in the reflection image generated by the image processing section 40; the spectral intensity of the illumination light stored in the measurement condition holding section 48; and the spectral sensitivity (sensitivity for each wavelength) of the imaging device 35 (step S301).

Next, a corrected value calculator 54 searches an estimated film-thickness providing the reflectance calculated in the step S301 from among the reflectance table 51; and calculates the corrected value for each wavelength from the estimated film-thickness obtained and an actual measured film-thickness held in the film-thickness data holding section 56 (step S302). The corrected value calculator 54 can perform, for example, the following process. That is, the corrected value calculator 54 finds film-thickness candidates (for example, C1 to C4), each of which corresponds to the intersection point between the reflectance curve corresponding to the wavelength $\lambda 1$ and the straight line indicating the actual reflectance of the wavelength $\lambda 1$ at the reference point; and the difference between one of the film-thickness candidates which is closest to an actual measurement value t of the geometric film-thickness and this actual measurement value t is determined as a corrected value $\delta_{\lambda 1}$ obtained when the film thickness is determined from the reflectance of the wavelength $\lambda 1$. Similarly, the corrected value calculator 54 calculates a corrected value $\delta$ corresponding to each wavelength while changing each of the illumination wavelengths.

Next, the reflectance calculator 52 calculates the reflectance for each wavelength based on the gradation value of each pixel included in the reflection image stored in an image storing section 47 for each of the wavelengths of the illumination lights in a similar manner as the step S301 (step S303). The reflectance calculated in the step S303 is used for the process of a candidate extracting section 53.

The candidate extracting section 53 extracts at least one of the film-thickness candidates for each wavelength by finding the intersection point between the reflectance calculated for each wavelength and the reflectance curve indicated by the reflectance data held in the reflectance table 51 (step S304).

The film-thickness candidate(s) extracted as described above is/are transferred to an error calculator 57 after a correction processing section 55 corrects the film-thickness candidate(s) by using the corrected value corresponding to each wavelength as described above (step S305).

Sets of the film-thickness candidates which have the number of elements k1, k2, k3 . . . respectively, namely, $\{C(\lambda 1)_1, \ldots, C(\lambda 1)_{k1}\}$, $\{C(\lambda 2)_1, \ldots, C(\lambda 2)_{k2}\}$, $\{C(\lambda 3)_1, \ldots, C(\lambda 3)_{k3}\}$, . . . are transferred from the correction processing section 55 to the error calculator 57 while corresponding to, for example, the respective wavelengths ($\lambda 1, \lambda 2, \lambda 3 \ldots$). In this case, the error calculator 57 calculates an error E expressed by the equation (Eq. 2) as shown below, for all of the potential combinations in a case of selecting each of the elements from among each of the sets, by using the film-thickness candidates ($C_{\lambda 1}, C_{\lambda 2}, C_{\lambda 3}, \ldots$) selected from each of the sets in each of the combinations (step S306).

$$E=(C_{\lambda 1}-C_{\lambda 2})^2+(C_{\lambda 2}-C_{\lambda 3})^2+(C_{\lambda 3}-C_{\lambda 1})^2+ \ldots \qquad (Eq.\ 2)$$

For example, in a case that four film-thickness candidates, namely, $\{C(\lambda i)_1, C(\lambda i)_2, C(\lambda 1)_3, C(\lambda i)_4\}$ (i=1 to 5) are obtained based on the reflectance corresponding to a target pixel of the reflection image taken with each of the illumination lights having the five types of wavelengths (for example, 546 nm, 436 nm, 405 nm, 313 nm, and 248 nm), the error calculator 57 calculates the error, for $4^5(=1024)$ combinations which are the potential combinations of the four film-thickness candidates, by using the equation (Eq. 2).

A determination processing section 58 receives a calculation result obtained by the error calculator; detects the combination of the film-thickness candidates having the smallest error value; and for example, specifies an average value of the film thickness candidates included in the combination as a film-thickness measurement value found from the reflectance (step S307). The film-thickness measurement value specified by the determination processing section 58 is held in the film-thickness data holding section 56 corresponding to the pixel position in the reflection image.

Here, it is judged as to whether or not the film-thickness measurement value is obtained for all of the pixels included in the reflection image of the wafer to be exposed (step S308). In a case that it is judged that the film-thickness measurement value is not obtained for all of the pixels, the processes of steps S303 to S307 are repeated for each pixel included in the reflection image.

On the other hand, in a case that it is judged that the film-thickness measurement value is obtained for all of the pixels, an inspection processing section 59 performs a continuous inspection process of film thickness distribution based on the film thickness distribution held in the film-thickness data holding section 56 (step S309). At first, the inspection processing section 59 finds, for example, the difference between the film-thickness measurement value t (xi, yi) obtained corresponding to the target pixel, which is indicated by the coordinates (xi, yi) and is included in the reflection image of the wafer to be exposed, and the film-thickness measurement value obtained corresponding to each of the pixels in the surroundings.

Subsequently, the difference between the film-thickness measurement value corresponding to the target pixel and the film-thickness measurement value corresponding to each of the pixels in the surroundings is compared with a predetermined threshold value. In a case that the difference is not more than the predetermined threshold value, the inspection processing section 59 judges that continuity is established between the film-thickness measurement value corresponding to the target pixel and the film-thickness measurement value corresponding to each of the pixels in the surroundings. Then, the inspection process is completed.

In a case that the difference between the film-thickness measurement value corresponding to the target pixel and the film-thickness measurement value corresponding to at least one of the pixels in the surroundings exceeds the predetermined threshold value, the inspection processing section 59 judges that the measurement value is an abnormal value departing from the target pixel and the correcting process of the measurement value of the film thickness is performed.

In this case, the inspection processing section 59 is capable of performing the following processes. That is, the inspection processing section 59 detects the combination having an error which is obtained by the error calculator 57 and is small next to that of the combination detected in the step S307; corrects the measurement value of film thickness using an average value of the film-thickness candidates included in the combination; and again inspects the continuity between the film-thickness measurement value corresponding to the target pixel and the film-thickness measurement value corresponding to each of the pixels in the surroundings.

In a case that the difference between the film-thickness measurement value corrected as described above and the film-thickness measurement value corresponding to each of the pixels in the surroundings is not more than the predetermined threshold value, the inspection processing section 59 writes the film-thickness measurement value corrected into the film-thickness data holding section 56. Then, the inspection process is completed.

By repeating the above processes for all of the pixels, it is possible to inspect the film-thickness data obtained by individually performing the fitting process for each of the pixels based on a result corresponding to each of the pixels in the vicinity of the target pixel; and to detect and correct the abnormal value.

After completing the inspection process, the film-thickness data, in which the abnormal value has been corrected, held in the film-thickness data holding section 56 is outputted to the image processing section 40 in the next step S310, and the film-thickness data is used for each of the processes executed by the image processing section 40.

Accordingly, since the specular image corresponding to the entire surface of the wafer to be exposed is obtained wholly and collectively for each of the illumination wavelengths, it is possible to obtain the reflectance data required for calculating the film-thickness in a short period of time. Therefore, it is possible to measure the film thickness distribution of the entire surface of the wafer in a very short period of time.

According to this embodiment, the image processing section 40 sets the focus condition or the dose amount for each of the optical exposers 60 subsequent to the second optical exposer, based on the information of the light from the surface of the FEM wafer 10*a* exposed by each of the optical exposers 60 subsequent to the second optical exposer, by using the data of the focus condition or dose amount set for the first optical exposer 60. Thus, it is possible to set the focus condition and/or the dose amount for each of the optical exposers 60 in a short period of time with a high degree of accuracy.

In particular, the image processing section 40 sets the focus condition and the dose amount for each of the optical exposers 60 subsequent to the second optical exposer based on the difference between the reference focus curve, which indicates the correlation between the variation of the focus and the variation of the luminance of the diffracted light in the first optical exposer 60, and the sample focus curve, which indicates the correlation between the variation of the focus and the variation of the luminance of the diffracted light in each of the optical exposers 60 subsequent to the second optical exposer. Thus, it is possible to easily set the focus condition and the dose amount for each of the optical exposers 60 subsequent to the second optical exposer in a short period of time. In this situation, by utilizing the image process of the pattern matching, it is possible to set the focus condition and the dose amount for each of the optical exposers 60 subsequent to the second optical exposer with high degree of accuracy.

The image processing section 40 finds the variation states of the focus and dose amount in the optical exposer 60 based on the difference between the condition focus curve, which indicates the correlation between the variation of the focus and the luminance of the diffracted light in the optical exposer 60 after the setting, and the reference focus curve used in the setting. Thus, it is possible to measure the variation states of the focus and dose amount in the optical exposers 60 (states of the plurality of optical exposers 60) in a short period of time. In this situation, by utilizing the image process of the pattern matching, it is possible to set the variation states of the focus and dose amount in the optical exposers 60 with high degree of accuracy.

The imaging device 35 takes the image of the entire surface of the wafer wholly and collectively, and thus it is possible to perform, for example, the settings and the like of the focus condition and dose amount in a shorter period of time.

In a case that the image by the diffracted light generated from the surface of the wafer is taken, it is hardly affected by the variation of the film thickness of the resist film and the like. Thus, it is possible to perform the settings of the focus condition and dose amount and the like with high degree of accuracy. In particular, the wavelength of a deep ultraviolet region such as 248 nm and 313 nm (j-ray) can be used for the wavelength of the illumination light.

In the embodiment described above, the following processes are also allowable. That is, the setting of the focus condition and the like is performed with higher degree of accuracy by selecting a portion at which the profile (line width) of the pattern is changed with a high sensitivity depending on the change of the focus irrespective of the change of the dose amount and finding the focus curve etc. Alternatively, the setting of the dose amount and the like is performed with higher degree of accuracy by selecting a portion at which the profile (line width) of the pattern is changed with a high sensitivity depending on the change of the dose amount irrespective of the change of the focus and finding the graph (dose curve) etc., indicating the change of the luminance (signal intensity) of the line pattern (vertical axis) with respect to the change of the dose amount (horizontal axis).

In the embodiment described above, the settings of the focus condition and dose amount and the like are performed by using the diffracted light generated on the surface of the wafer. However, the present teaching is not limited thereto; and it is allowable to use, for example, change(s) of the state(s) of the specular light and/or the polarized light generated on the surface of the wafer.

Figure 4:
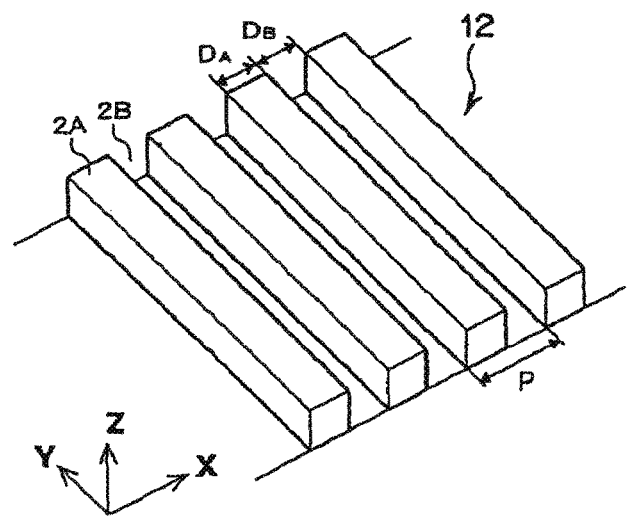
FIG. 4 is a perspective view for explaining a concavo-convex structure of a repetitive pattern.

Next, an explanation will be made with respect to the case of carrying out the PER inspection of the surface of the wafer 10 by the surface inspection apparatus 1. Noted that the repetitive pattern 12 is supposed to be, as shown in FIG. 4, a resist pattern (line pattern) where a plurality of line portions 2A are aligned with a certain pitch P along the short direction (X-direction). Further, there is a space portion 2B between adjacent line portions 2A. Further, the direction of aligning the line portions 2A (X-direction) will be referred to as the "repetitive direction of the repetitive pattern 12".

Here, the design value of line width $D_A$ of each of the line portions 2A in the repetitive pattern 12 is supposed to be ½ of the pitch P. When the repetitive pattern 12 is formed just as following the design value, then the line width $D_A$ of each of the line portions 2A is equal to the line width $D_B$ of each of the space portions 2B, and the volume ratio between the line portion 2A and the space portion 2B is substantially 1:1. On the other hand, when the exposure focus (or dose amount) deviates from an appropriate value in forming the repetitive pattern 12, then the pitch P does not change but the line width $D_A$ of each of the line portions 2A differs from the design value and from the line width $D_B$ of each of the space portions 2B and, as a result, the volume ratio between the line portion 2A and the space portion 2B deviates from substantially 1:1.

The PER inspection utilizes the change in the volume ratio between the line portion 2A and the space portion 2B in the repetitive pattern 12 as described above to carry out abnormity inspection of the repetitive pattern 12. Further, in order to simplify explanation, the ideal volume ratio (design value) is supposed to be 1:1. The change in volume ratio is because the exposure focus (or does amount) deviates from the appropriate value, and appears in each shot region of the wafer 10. Further, it is possible to rephrase the volume ratio as the area ratio of cross-section shape.

Figure 5:
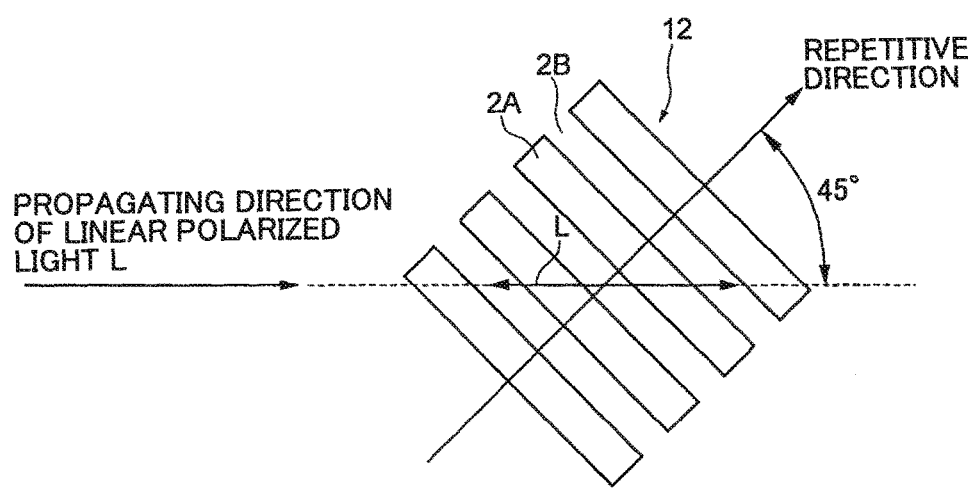
FIG. 5 is a diagram for explaining a state of inclination between an incidence surface of a linear polarized light and a repetitive direction of a repetitive pattern.

In the PER inspection, as shown in FIG. 2, the illumination-side polarizing filter 26 and the light-receiving-side polarizing filter 32 are inserted into the optical path. Further, when carrying out the PER inspection, the stage 5 tilts the wafer 10 at an inclination angle such that the light receiving system 30 can receive the specular light from the wafer 10 irradiated by the illumination light. Further, the stage 5 stops at a predetermined rotation position to maintain the repetitive direction of the repetitive pattern 12 in the wafer 10 as 45 degrees oblique to the oscillation direction of the illumination light (linear polarized light L) on the surface of the wafer 10 as shown in FIG. 5. This is because the amount of light for inspecting the repetitive pattern 12 is maximized. Further, when the angle is set to be 22.5 degrees or 67.5 degrees, the sensitivity of inspection is enhanced. The angle is not limited to these degrees but can be set in arbitrary angular directions.

The illumination-side polarizing filter 26 is provided between the light guiding fiber 24 and the illumination-side concave mirror 25, and its transmission axis is set in a predetermined azimuth direction to extract the linear polarized light from the light emitted from the illumination unit 21 according to the transmission axis. At this time, because the exit portion of the light guiding fiber 24 is arranged in the focal position of the illumination-side concave mirror 25, the illumination-side concave mirror 25 makes the light transmitted through the illumination-side polarizing filter 26 be a parallel light beam to irradiate the wafer 10 as a semiconductor substrate. In this manner, the light exiting the light guiding fiber 24 becomes the linear polarized light L of p-polarization (see FIG. 5) via the illumination-side polarizing filter 26 and the illumination-side concave mirror 25 to irradiate the entire surface of the wafer 10 as the illumination light.

At this time, because the propagating direction of the linear polarized light L (the direction of the main light of the linear polarized light L reaching any points on the surface of the wafer 10) is approximately parallel to the optical axis, the incidence angle of the linear polarized light L at each point of the wafer 10 is identical to each other due to the parallelity. Further, because the linear polarized light L incident on the wafer 10 is p-polarized, as shown in FIG. 5, when the repetitive direction of the repetitive pattern 12 is set at a 45-degree angle to the incidence surface of the linear polarized light L (the propagating direction of the linear polarized light L on the surface of the wafer 10), the angle formed between the oscillation direction of the linear polarized light L on the surface of the wafer 10 and the repetitive direction of the repetitive pattern 12 is also set at 45 degrees. In other words, the linear polarized light L enters the repetitive pattern 12 such that the oscillation direction of the linear polarized light L on the surface of the wafer 10 is inclined 45 degrees with respect to the repetitive direction of the repetitive pattern 12 and that the linear polarized light L obliquely traverses the repetitive pattern 12.

The specular light reflected by the surface of the wafer 10 is condensed by the light-receiving-side concave mirror 31 of the light receiving system 30 and reaches the imaging plane of the imaging device 35. At this time, the polarization state of the linear polarized light L changes due to the form birefringence in the repetitive pattern 12. The light-receiving-side polarizing filter 32 is provided between the light-receiving-side concave mirror 31 and the imaging device 35, and the azimuth of the transmission axis of the light-receiving-side polarizing filter 32 is set to be perpendicular to the transmission axis of the illumination-side polarizing filter 26 described above (a crossed Nichol state). Therefore, the light-receiving-side polarizing filter 32 can extract the polarized component (the s-polarized component, for example) almost orthogonal in the oscillation direction to the linear polarized light L in the specular light from the wafer 10 (the repetitive pattern 12) to lead the same to the imaging device 35. As a result, on the imaging plane of the imaging device 35, the reflection image of the wafer 10 is formed by the polarized component almost orthogonal in the oscillation direction to the linear polarized light L in the specular light from the wafer 10.

In order for the surface inspection apparatus 1 to carry out the PER inspection of the surface of the wafer 10, first, as shown in FIG. 2, the illumination-side polarizing filter 26 and the light-receiving-side polarizing filter 32 are inserted into the optical path, and the wafer 10 is carried onto the stage 5 by the carrier device (not shown). Further, it is possible to place the wafer 10 on the stage 5 in predetermined position and direction since the alignment mechanism (not shown) acquires positional information of the pattern formed in the surface of the wafer 10 in carrying. Further, at this time, the stage 5 tilts the wafer 10 at an inclination angle such that the light receiving system 30 can receive the specular light from the wafer 10 irradiated by the illumination light. Further, the stage 5 stops at a predetermined rotation position to maintain the repetitive direction of the repetitive pattern 12 in the wafer 10 as 45 degrees oblique to the oscillation direction of the illumination light (linear polarized light L) on the surface of the wafer 10.

Next, the surface of the wafer 10 is irradiated with the illumination light. When irradiating the surface of the wafer 10 with the illumination light under such a condition, the light exiting from the light guiding fiber 24 of the illumination unit 21 becomes the linear polarized light L of P-polarization via the illumination-side polarizing filter 26 and the illumination-side concave mirror 25 to irradiate the entire surface of the wafer 10 as the illumination light. The specular light reflected by the surface of the wafer 10 is condensed by the light-receiving-side concave mirror 31, and reaches the imaging plane of the imaging device 35 to form a (reflection) image of the wafer 10.

At this time, the polarization state of the linear polarized light L changes due to the form birefringence in the repetitive pattern 12. The light-receiving-side polarizing filter 32 can extract the polarized component (namely, the change in the polarization state of the linear polarized light L) almost orthogonal in the oscillation direction to the linear polarized light L in the specular light from the wafer 10 (the repetitive pattern 12) to lead the same to the imaging device 35. As a result, a reflection image of the wafer 10 is formed on the imaging plane of the imaging device 35, by the polarized component almost orthogonal in the oscillation direction to the linear polarized light L in the specular light from the wafer 10.

Here, the imaging device 35 photoelectrical converts the surface image (reflection image) of the wafer 10 formed on the imaging plane to generate an image signal, and outputs the image signal to the image processing section 40. The image processing section 40 generates a digital image of the wafer 10 based on the image signal of the wafer 10 inputted from the imaging device 35. After generating the image (digital image) of the wafer 10, the image processing section 40 compares the image data of the wafer 10 with the image data of nondefective wafers to inspect whether or not there is any defect (abnormity) in the surface of the wafer 10. Since luminance information (signal intensity) of the reflection image of nondefective wafers is conceivably to show the maximum luminance value, for example, "abnormity" is determined when the change in luminance compared with nondefective wafers is greater than a predetermined threshold value (allowable value), while "normality" is determined when it is less than the threshold value. Then, the inspection result from the image processing section 40 and the image of the relevant wafer 10 are outputted and displayed on the image display device (not shown).

The image processing section 40 is capable of finding the reference focus curve and the sample focus curve by the polarized light for the optical exposer 60 by utilizing the image of a developed wafer exposed under the condition of changing the focus and dose amount of the optical exposer 60 for each shot. Then, in a case that respective moving amounts in the directions of the horizontal axis and the vertical axis generated when the reference focus curve is fitted to the sample focus curve are found, it is possible to set the optimal focus condition and dose amount for each of the optical exposers 60 subsequent to the second optical exposer in a short period of time with a high degree of accuracy in the same manner as in the case of the diffracted light. In particular, it is allowable to perform the following processes in the step S105 of the flowchart shown in FIG. 6. That is, the linear polarized light L as the illumination light is irradiated to the surface of the FEM wafer 10a; the imaging device 35 photoelectrical converts the reflection image of the FEM wafer 10a to generate the image signal; and the image signal is outputted to the image processing section 40.

In a case that the illumination and the imaging of the wafer and the like are performed in the same manner as in the case of the PER inspection, the image processing section 40 is capable of finding the condition focus curve by the polarized light of the optical exposer 60. Thus, it is possible to measure the variation states of the focus and dose amount for the plurality of optical exposers 60 after the setting in a short period of time with a high degree of accuracy. In particular, it is allowable to perform the following processes in the step S201 of the flowchart shown in FIG. 7. That is, the linear polarized light L as the illumination light is irradiated to the surface of the FEM wafer 10a; the imaging device 35 photoelectrical converts the reflection image of the FEM wafer 10a to generate the image signal; and the image signal is outputted to the image processing section 40.

In the above embodiment, it is used the developed FEM wafer 10a exposed under the condition of changing the focus and dose amount of the optical exposer 60 for each shot. However, the present teaching is not limited thereto. It is possible to use developed wafers each exposed under the condition of changing the focus and dose amount of the optical exposer 60 for each of the wafers.

In the above embodiment, it is performed the setting with respect to the same process for the plurality of optical exposers 60 (the devices are individually different from one another). However, the present teaching is not limited thereto. For example, the present teaching is applicable to a case as follows. That is, for example, after performing the setting with respect to a predetermined process for one optical exposer 60, setting with respect to another process is performed for the one optical exposer 60. Then, setting with respect to the same process as the predetermined process is again performed for the one optical exposer 60 at time different from the time at which the setting with respect to the predetermined setting is performed first.

In the above embodiment, it is measured the film thickness of the thin film (resist film) formed on the surface of the wafer to be exposed. However, the present teaching is not limited thereto. It is allowable to measure the film thickness of the thin film on the surface of the exposed wafer.

As a construction of the inspection apparatus, the following construction is also allowable. For example, the inspection apparatus is provided with a stage which supports a semiconductor substrate which is exposed by an optical exposer to have a predetermined pattern formed on a film of a surface thereof; an irradiation section which irradiates the surface of the semiconductor substrate supported by the stage with an illumination light; a detector which detects a light from the surface of the semiconductor substrate to which the illumination light is irradiated; a setting calculator which calculates, by using a focus condition as a reference or an exposure amount as a reference set in the optical exposer, based on information of the light, detected by the detector, from the surface of the semiconductor substrate exposed by another optical exposer which is temporally or individually different from the optical exposer, an adjustment value of a focus condition or an exposure amount for the another optical exposer which is temporally or individually different from the optical exposer; and a film-thickness measurer which measures a film thickness of the film on the surface of the semiconductor substrate exposed by each of the optical exposer and the another optical exposer which is temporally or individually different from the optical exposer. The setting calculator can be configured to perform correction of the adjustment value based on each film thickness measured by the film-thickness measurer.

It is possible that the inspection apparatus as described above further includes a storing section in which there is stored a first correlation which is a correlation between a variation of the focus condition or the exposure amount in the optical exposer and a variation of the luminance from the pattern formed by being exposed by the optical exposer. Further, it is possible that the setting calculator finds a second correlation based on information of the light, detected by the detector, from the surface of the semiconductor substrate exposed by the another optical exposer which is temporally or individually different from the optical exposer while changing the focus condition or the exposure amount for each shot. Wherein the second correlation is a correlation between a variation of the focus condition and the exposure amount in the another optical exposer which is temporally or individually different from the optical exposer and a variation of the luminance from the pattern formed by being exposed by the another optical exposer which is temporally or individually different from the optical exposer. Then it is possible that the setting calculator calculates the adjustment value based on the difference between the second correlation and the first correlation stored in the storing section.

In the inspection apparatus as described above, it is possible to find the difference between the second correlation and the first correlation by using the image process of the pattern matching.

In the inspection apparatus as described above, in a case that the setting calculator calculates the adjustment value, it is possible that the illuminator irradiates, with the illumination light, the surface of the semiconductor substrate exposed by the another optical exposer which is temporally or individually different from the optical exposer so that a diffracted light is generated on the pattern of the semiconductor substrate exposed by the another optical exposer which is temporally or individually different from the optical exposer; that the detector detects the diffracted light generated on the pattern of the semiconductor substrate to which the illumination light is irradiated; and that the setting calculator calculates the adjustment value based on information of the diffracted light detected by the detector. In a case that the film-thickness measurer measures the film thickness, it is possible that the illuminator irradiates, with the illumination light, the surface of the semiconductor substrate exposed by each of the optical exposer and the another optical exposer which is temporally or individually different from the optical exposer; that the detector detects a specular light from the surface of the semiconductor substrate to which the illumination light is irradiated; and that the film-thickness measurer measures the film thickness based on information of the specular light detected by the detector.

In the inspection apparatus as described above, in a case that the setting calculator calculates the adjustment value, the illuminator can irradiate, with an approximately-linearly-polarized light as the illumination light, the surface of the semiconductor substrate exposed by the another optical exposer which is temporally or individually different from the optical exposer; the detector can detect change of the approximately-linearly-polarized light due to form birefringence in the pattern of the semiconductor substrate to which the approximately-linearly-polarized light is irradiated; the setting calculator can calculate the adjustment value from the change of the approximately-linearly-polarized light detected by the detector. In a case that the film-thickness measurer measures the film thickness, the illuminator can irradiate, with the illumination light, the surface of the semiconductor substrate exposed by each of the optical exposer and the another optical exposer which is temporally or individually different from the optical exposer; the detector can detect a specular light from the surface of the semiconductor substrate to which the illumination light is irradiated; and the film-thickness measurer can measure the film thickness based on information of the specular light detected by the detector.

What is claimed is:

1. An inspection apparatus comprising:
   an illuminator configured to irradiate a pattern formed by an exposure with an illumination light;
   a detector configured to detect intensity of a reflected light from the pattern to which the illumination light is irradiated; and
   a setting calculator connected to the detector communicably and configured to calculate a difference of exposure conditions between a first optical exposure apparatus and a second optical exposure apparatus based on first information and second information, wherein the first information is related to a change of detected amounts of the intensity of the reflected light, from a first plurality of patterns, with respect to a change of exposure conditions of the first optical exposure apparatus, each of the first plurality of patterns being formed by the first optical exposure apparatus by varying exposure conditions of the first optical exposure apparatus, wherein the second information is related to a change of detected amounts of the intensity of the reflected light, from a second plurality of patterns, with respect to a change of exposure conditions of the second optical exposure apparatus, each of the second plurality of patterns being formed by the second optical exposure apparatus by varying exposure conditions of the second optical exposure apparatus, and wherein the setting calculator outputs information for setting exposure conditions, including at least one of a focus and an exposure amount, of one of the first optical exposure apparatus and the second optical exposure apparatus, the information being based on the difference of exposure conditions between the first optical exposure apparatus and the second optical exposure apparatus, and wherein the setting calculator is configured to output the information to at least one of the first or second optical exposure apparatuses, or to a computer which is communicably connected to at least one of the first or second optical exposure apparatuses.

2. The inspection apparatus according to claim 1, wherein the apparatus is further comprising a memory configured to store the first information, wherein the deviation between the first information and the second information is calculated based on the first information stored in the memory.

3. The inspection apparatus according to claim 1, wherein an image processor compares the first information with the second information by a pattern matching between a curve illustrated by the first information and a curve illustrated by the second information.

4. The inspection apparatus according to claim 1, wherein first exposure conditions set to the first optical exposure apparatus are determined based on a measurement result of a profile of the pattern.

5. The inspection apparatus according to claim 1, wherein the first plurality of patterns, which is formed under the first exposure conditions by the first optical exposure apparatus, including at least one lens, adjusted based on the deviation calculated, is illuminated to find the first information.

6. The inspection apparatus according to claim 1, wherein the intensity of the reflected light is detected by the detector at a plurality of portions in the first plurality of patterns formed by one exposure of the first optical exposure apparatus or at a plurality of portions in the second plurality of patterns formed by one exposure of the second optical exposure apparatus.

7. The inspection apparatus according to claim 1, wherein the illuminator irradiates wholly an entire surface of a substrate on which the first plurality of patterns or the second plurality of patterns are formed with the illumination light which is a substantially parallel light beam, and the detector detects a light from the entire surface of the substrate to which the illumination light is irradiated wholly and collectively.

8. The inspection apparatus according to claim 1, wherein the detector detects a diffracted light, which is generated on the first plurality of patterns or the second plurality of patterns by irradiating the first plurality of patterns or the second plurality of patterns with the illumination light.

9. The inspection apparatus according to claim 1, wherein the illuminator irradiates the surface of a substrate with a substantially linearly-polarized light as the illumination light; and the detector detects a polarized component in an oscillation direction which is substantially orthogonal to an oscillation direction of the substantially linearly-polarized light reflected by the substrate.

10. The inspection apparatus according to claim 1, wherein the setting calculator corrects the difference between the first information and the second information based on film thickness of a resist film on which the first plurality of patterns or the second plurality of patterns are formed.

11. The inspection apparatus according to claim 10, wherein the film thickness is based on a specular light from the resist film illuminated by the illumination light of the illuminator.

12. The inspection apparatus according to claim 10, wherein the specular light includes a plurality of specular lights from the resist film illuminated by illumination lights having a plurality of wavelengths and the film thickness is based on each of the specular lights.

13. An inspection method, comprising:

illuminating a pattern formed by an exposure with an illumination light;

detecting intensity of a reflected light from the pattern to which the illumination light is irradiated;

calculating a difference of exposure conditions between a first optical exposure apparatus and a second optical exposure apparatus based on first information and second information, wherein the first information is related to a change of detected amounts of the intensity of the reflected light, from a first plurality of patterns, with respect to a change of exposure conditions of the first exposure apparatus, each of the first plurality of patterns being formed by the first optical exposure apparatus by varying exposure conditions of the first optical exposure apparatus, wherein the second information is related to a change of detected amounts of the intensity of the reflected light, from a second plurality of patterns, with respect to a change of exposure conditions of the second optical exposure apparatus, each of the second plurality of patterns being formed by the second optical exposure apparatus by varying exposure conditions of the second optical exposure apparatus, and wherein information, which is for setting exposure conditions, including at least one of a focus and an exposure amount, of one of the first optical exposure apparatus and the second optical exposure apparatus, and which is based on the difference of exposure conditions between the first optical exposure apparatus and the second optical exposure apparatus is output to at least one of the first or second optical exposure apparatuses, or to a computer which is communicably connected to at least one of the first or second optical exposure apparatuses.

14. The inspection method according to claim 13, wherein each of the exposure conditions of the first optical exposure apparatus and the exposure conditions of the second optical exposure apparatus is at least one of a focus and an exposure amount.

15. The inspection method according to claim 13, wherein the deviation is found by using a pattern matching between a curve illustrated by the first approximated function and the second approximated function.

16. The inspection method according to claim 13, wherein the intensity of the reflected light is detected at a plurality of portions in the first plurality of patterns formed by one exposure of the first optical exposure apparatus or at a plurality of portions in the second plurality of patterns formed by one exposure of the second optical exposure apparatus.

17. The inspection method according to claim 13, wherein information based on the difference of exposure conditions between the first optical exposure apparatus and the second optical exposure apparatus is output outputted to the second optical exposure apparatus by which the second plurality of patterns is formed under the exposure conditions of the second optical exposure apparatus.

18. The inspection method according to claim 13, wherein the difference of exposure conditions between the first optical exposure apparatus and the second optical exposure apparatus is corrected based on a film thickness of a resist film before the pattern is exposed.

19. The inspection method according to claim 18, wherein the film thickness is found based on a specular light from the resist film illuminated.

20. The inspection method according to claim 18, wherein the illumination light has a plurality of illumination lights having a plurality of wavelengths, and
the resist film is irradiated with each of the plurality of illumination lights to find the film thickness based on a specular light from the resist film by each of the plurality of illumination lights.

21. The inspection apparatus according to claim 1, wherein both the parameter of the exposure conditions of the first optical exposure apparatus and the parameter of the exposure conditions of the second optical exposure apparatus are at least one of a focus and an exposure amount.

22. The inspection apparatus according to claim 1, wherein a range of the exposure conditions of the first optical exposure apparatus overlaps with at least a part of a range of the exposure conditions of the second optical exposure apparatus.

23. An inspection apparatus comprising:
an illuminator configured to irradiate a pattern formed by an exposure with an illumination light;
a detector configured to detect amount of intensity of a reflected light from the pattern to which the illumination light is irradiated; and
a processor connected to the detector communicably and configured to:
calculate a difference of exposure conditions between a first exposure by an optical exposure apparatus and a second exposure by the optical exposure apparatus based on first information and second information,
wherein the first information is related to a change of detected amounts of the intensity of the reflected light, from a first plurality of patterns with respect to a change of exposure conditions of the optical exposure apparatus, each of the first plurality of patterns being formed by the optical exposure apparatus by varying exposure conditions of the optical exposure apparatus,
wherein the second information is related to a change of detected amounts of the intensity of the reflected light, from a second plurality of patterns, with respect to a change of exposure conditions of the optical exposure apparatus, each of the second plurality of patterns being formed by the optical exposure apparatus, after elapse of a certain period of time from forming the first plurality of patterns, by varying exposure conditions of the optical exposure apparatus, and
wherein the processor outputs information for setting exposure conditions, including at least one of a focus and an exposure amount, of the optical exposure apparatus, the information being based on the difference of exposure conditions between the first exposure and the second exposure,
wherein the processor is configured to output the information to the optical exposure apparatus, or to a computer which is communicably connected to the optical exposure apparatus.

24. An inspection method, comprising:
illuminating a pattern formed by an exposure with an illumination light;
detecting intensity of a reflected light from the pattern to which the illumination light is irradiated; and
calculating a difference of exposure conditions between a first exposure by an optical exposure apparatus and a second exposure by the optical exposure apparatus based on first information and second information,
wherein the first information is related to a change of detected amounts of the intensity of the reflected light, from a first plurality of patterns, with respect to a change of exposure conditions of the optical exposure apparatus, each of the first plurality of patterns being formed by the optical exposure apparatus by varying exposure conditions of the optical exposure apparatus,
wherein the second information is related to a change of detected amounts of the intensity of the reflected light, from a second plurality of patterns, with respect to a change of exposure conditions of the optical exposure apparatus, each of the second plurality of patterns being formed by the optical exposure apparatus, after elapse of a certain period of time from forming the first plurality of patterns, by varying exposure conditions of the optical exposure apparatus, and
wherein information which is for setting exposure conditions, including at least one of a focus and an exposure amount, of the optical exposure apparatus, and which is based on the difference of exposure conditions between the first exposure and the second exposure is output to the optical exposure apparatus, or to a computer which is communicably connected to the optical exposure apparatus outputted.

25. The inspection apparatus according to claim 1,
wherein the setting calculator is configured to use a first approximated function, as the first information, which is obtained by a function fitting between the change of detected amounts of the intensity of the reflected light from the first plurality of patterns and the change of the exposure conditions of the first optical exposure apparatus, and
wherein the setting calculator is configured to use a second approximated function, as the second information, which is obtained by a function fitting between the change of detected amounts of the intensity of the reflected light from the second plurality of patterns and the change of the exposure conditions of the second optical exposure apparatus.

26. The inspection method according to claim 13,
wherein a first approximated function is used as the first information, which is obtained by a function fitting between the change of detected amounts of the intensity of the reflected light from the first plurality of patterns and the change of the exposure conditions of the first optical exposure apparatus, and
wherein a second approximated function is used as the second information, which is obtained by a function fitting between the change of detected amounts of the intensity of the reflected light from the second plurality of patterns and the change of the exposure conditions of the second optical exposure apparatus.

27. The inspection apparatus according to claim 23,
wherein the processor is configured to use a first approximated function, as the first information, which is obtained by a function fitting between the change of detected amounts of the intensity of the reflected light from the first plurality of patterns and the change of the exposure conditions of the optical exposure apparatus, and
wherein the processor is configured to use a second approximated function, as the second information, which is obtained by a function fitting between the change of detected amounts of the intensity of the reflected light from the second plurality of patterns and the change of the exposure conditions of the optical exposure apparatus.

28. The inspection method according to claim 24,
wherein a first approximated function is used as the first information, which is obtained by a function fitting between the change of detected amounts of the intensity of the reflected light from the first plurality of patterns and the change of the exposure conditions of the optical exposure apparatus, and
wherein a second approximated function is used as the second information, which is obtained by a function fitting between the change of detected amounts of the intensity of the reflected light from the second plurality of patterns and the change of the exposure conditions of the optical exposure apparatus.

29. The inspection apparatus according to claim 25, wherein the setting calculator is configured to calculate the difference of exposure conditions between the first optical exposure apparatus and the second optical exposure apparatus by comparing the first approximated function and the second approximated function.

30. The inspection method according to claim 26, wherein the difference of exposure conditions between the first optical exposure apparatus and the second optical exposure apparatus is calculated by comparing the first approximated function and the second approximated function.

31. The inspection apparatus according to claim 27, wherein the processor is configured to calculate the difference of exposure conditions due to a change of the exposure condition of the optical exposure apparatus after elapse of the certain period of time from forming the patterns by comparing the first approximated function and the second approximated function.

32. The inspection method according to claim 28, wherein the difference of exposure conditions due to a change of the exposure condition of the optical exposure apparatus after elapse of the certain period of time from forming the patterns is calculated by comparing the first approximated function and the second approximated function.

* * * * *

UNITED STATES PATENT AND TRADEMARK OFFICE
CERTIFICATE OF CORRECTION

PATENT NO. : 10,359,367 B2
APPLICATION NO. : 13/663911
DATED : July 23, 2019
INVENTOR(S) : Fukazawa Page 1 of 1

It is certified that error appears in the above-identified patent and that said Letters Patent is hereby corrected as shown below:

In the Claims

Claim 17, Column 25, Line 18, "apparatus is output outputted to" should read -- apparatus is output to --.

Signed and Sealed this
Twenty-sixth Day of November, 2019

Andrei Iancu
*Director of the United States Patent and Trademark Office*